US011116212B2

(12) United States Patent
Gilbert

(10) Patent No.: US 11,116,212 B2
(45) Date of Patent: Sep. 14, 2021

(54) **CARBONYL CONTAINING COMPOUNDS FOR CONTROLLING AND REPELLING *CIMICIDAE* POPULATIONS**

(75) Inventor: Michael Gilbert, Vancouver (CA)

(73) Assignee: SemiosBio Technologies Inc., Vancouver (CA)

( * ) Notice: Subject to any disclaimer, the term of this patent is extended or adjusted under 35 U.S.C. 154(b) by 810 days.

(21) Appl. No.: 14/114,146

(22) PCT Filed: Mar. 29, 2012

(86) PCT No.: PCT/CA2012/050203
§ 371 (c)(1),
(2), (4) Date: Dec. 19, 2013

(87) PCT Pub. No.: WO2012/129702
PCT Pub. Date: Oct. 4, 2012

(65) Prior Publication Data
US 2014/0105952 A1    Apr. 17, 2014

Related U.S. Application Data

(60) Provisional application No. 61/479,000, filed on Apr. 26, 2011, provisional application No. 61/592,691, filed on Jan. 31, 2012.

(51) Int. Cl.

| | | |
|---|---|---|
| *A01N 37/02* | (2006.01) |
| *A01N 35/02* | (2006.01) |
| *A01N 37/18* | (2006.01) |
| *A01N 37/42* | (2006.01) |
| *A01N 43/08* | (2006.01) |
| *A61K 31/225* | (2006.01) |
| *A61K 31/22* | (2006.01) |
| *A61K 31/13* | (2006.01) |
| *A01N 49/00* | (2006.01) |
| *A61K 31/341* | (2006.01) |
| *A01N 37/14* | (2006.01) |
| *A61K 31/11* | (2006.01) |
| *A61K 31/16* | (2006.01) |
| *A01N 37/20* | (2006.01) |
| *A01N 37/04* | (2006.01) |

(52) U.S. Cl.
CPC ............ *A01N 37/02* (2013.01); *A01N 35/02* (2013.01); *A01N 37/04* (2013.01); *A01N 37/14* (2013.01); *A01N 37/18* (2013.01); *A01N 37/20* (2013.01); *A01N 37/42* (2013.01); *A01N 43/08* (2013.01); *A01N 49/00* (2013.01); *A61K 31/11* (2013.01); *A61K 31/13* (2013.01); *A61K 31/16* (2013.01); *A61K 31/22* (2013.01); *A61K 31/225* (2013.01); *A61K 31/341* (2013.01)

(58) Field of Classification Search
CPC ........ A01N 37/20; A01N 37/42; A01N 49/00; A01N 37/02; A01N 37/14; A01N 37/04; A01N 35/02; A01N 37/18; A01N 43/08; A61K 31/11; A61K 31/13; A61K 31/16; A61K 31/22; A61K 31/225; A61K 31/341
See application file for complete search history.

(56) References Cited

U.S. PATENT DOCUMENTS

| | | | |
|---|---|---|---|
| 6,420,182 B1 * | 7/2002 | Start ...................... G01N 33/84 436/163 |
| 7,288,573 B2 | 10/2007 | Roe ............................... 514/675 |
| 7,378,557 B1 | 5/2008 | Zhang ........................... 568/342 |
| 7,892,528 B2 | 2/2011 | Siljander et al. ............... 424/84 |
| 2007/0044372 A1 * | 3/2007 | Lang ..................... A01M 1/023 43/114 |
| 2008/0193387 A1 * | 8/2008 | De Wolff ............... A61K 36/23 424/47 |
| 2011/0072711 A1 * | 3/2011 | Black .................. A01M 1/2033 43/123 |
| 2011/0099886 A1 | 5/2011 | Siljander et al. ............... 43/121 |
| 2011/0229589 A1 * | 9/2011 | Elraz ...................... A01N 65/44 424/742 |
| 2011/0289824 A1 | 12/2011 | Wu et al. ..................... 43/132.1 |
| 2012/0046359 A1 * | 2/2012 | Bedoukian ............. A01N 35/06 514/530 |

FOREIGN PATENT DOCUMENTS

| | | |
|---|---|---|
| JP | 2002308864 | 10/2002 |
| WO | WO2010/090818 | 8/2010 |
| WO | WO2010/126576 | 11/2010 |
| WO | WO-2010126576 A1 * | 11/2010 ............. A01N 49/00 |

OTHER PUBLICATIONS

Harraca, Vincent, Camilla Ryne, and Rickard Ignell. "Nymphs of the common bed bug (*Cimex lectularius*) produce anti-aphrodisiac defence against conspecific males." BMC biology 8.1 (2010): 1-7. (Year: 2010).*
Benoit, Joshua et al. "Addition of Alarm Pheromone Components Improves the Effectiveness of Desiccant Dusts Against Cimex Lectularius", J. Med. Entomol., vol. 46(3), 572-579, (2009) pp. 1-13.
EESR & Search Opinion for European Patent Application No. 12765792.2 dated Feb. 20, 2015.
Harraca, Vincent et al. "Nymphs of the common bed bug (*Cimex lectularius*) produce anti-aphrodisiac defence against conspecific males", BMC Biology, vol. 8(121), (2010), pp. 1-7.

(Continued)

*Primary Examiner* — Abigail Vanhorn
(74) *Attorney, Agent, or Firm* — Smiths IP; Paul Smith

(57) ABSTRACT

Compositions and methods for controlling and/or repelling bedbugs are provided. The compositions comprise one or more compounds having bedbug repellant activity. Such compounds may be, for example, naturally occurring semiochemicals or structural or functional analogs of naturally occurring semiochemicals. Exemplary compounds are compounds of general formula (I).

6 Claims, 1 Drawing Sheet

(56) References Cited

OTHER PUBLICATIONS

International Search Report & Written Opinion dated Aug. 2, 2012.
Morales-Sanfrutos, J. et al. "Alkyl sulfonyl derivatized PAMAM-G2 dendrimers as nonviral gene delivery vectors with improved transfection effciencies", Organic & Biomolecular Chemistry, vol. 9, (2011), pp. 851-864.
Office Action for Chinese Patent Application No. 201280031360.7 dated Oct. 27, 2014.
Office Action for New Zealand Patent Application No. 616966 dated Jul. 31, 2014.
Siljander, Eric et al. "Identification of the airbourne aggregation pheromone of the common bed bug, *Cimenx lectularius*", J Chem. Ecol., (2008), 34(6), pp. 708-718.
Weeks, Emma et al. "Semiochemicals of the common bed bug, *Cimex lectularius* L. (Hemiptera: Cimicidae), and their potential for use in monitoring and control", Pest Manag. Sci., vol. 67, (2011), pp. 10-20.

\* cited by examiner

A.
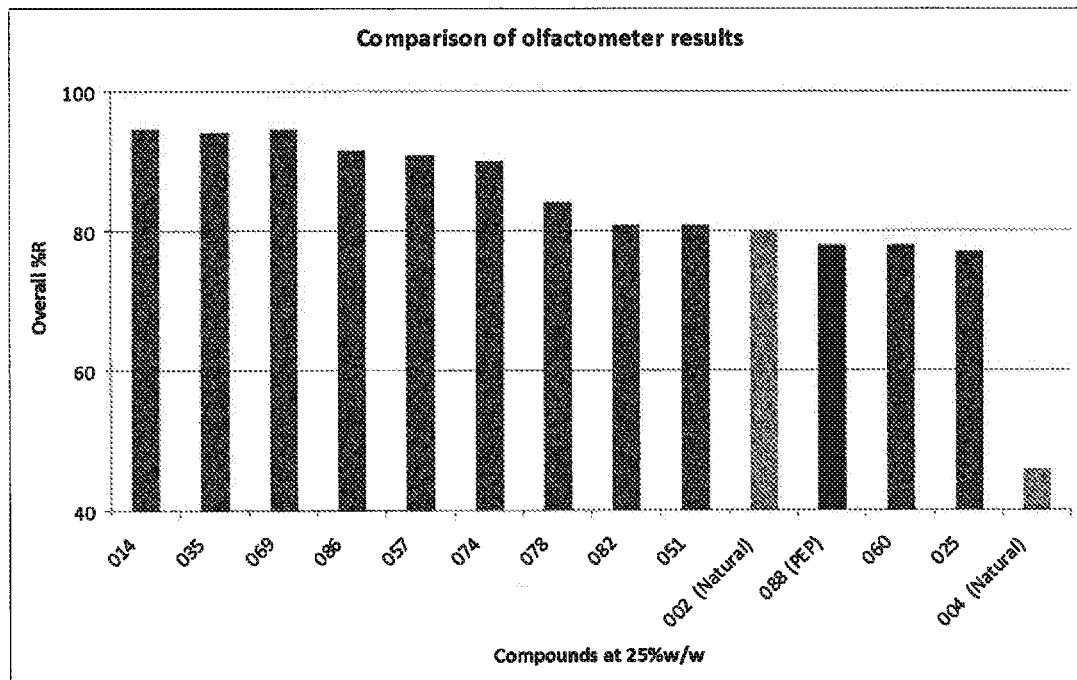
B.
| Compound at 25% w/w | Overall %Repellency |
|---|---|
| 014 | 94 |
| 035 | 94 |
| 069 | 94 |
| 086 | 92 |
| 057 | 91 |
| 074 | 90 |
| 078 | 84 |
| 082 | 81 |
| 051 | 81 |
| 002 (Natural) | 80 |
| 088 (PEP) | 78 |
| 060 | 78 |
| 025 | 77 |
| 004 (Natural) | 46 |

CARBONYL CONTAINING COMPOUNDS FOR CONTROLLING AND REPELLING *CIMICIDAE* POPULATIONS

CROSS-REFERENCE TO RELATED APPLICATIONS

The present application is a national phase application under 35 U.S.C. § 371 of International Patent Application No. PCT/CA2012/050203, filed 29 Mar. 2012, which claims priority to U.S. Provisional Patent Application Nos. 61/479,000, filed 26 Apr. 2011 and 61/592,691, filed 31 Jan. 2012. The entire contents of these applications are incorporated by reference.

FIELD OF THE INVENTION

The present invention relates to the field of pest control and, in particular, to compositions and methods for controlling, detecting and/or repelling bedbugs.

BACKGROUND OF THE INVENTION

Bedbugs (*Cimicidae*) are parasitic insects that feed exclusively on warm-blooded animals. The most common type is *Cimex lectarius*. Bedbugs have been known human parasites for thousands of years and the insect's preferred habitat includes beds or other areas where people sleep. Bedbugs are essentially nocturnal and are capable of feeding unnoticed on their hosts. A number of health effects may occur due to bedbugs including skin rashes, psychological effects and allergic symptoms. Bedbugs were largely eradicated in the 1940s by pesticides such as DDT. However, since the 1990, the prevalence of bedbugs and associated health effects have been on the rise, owing to greater foreign travel, more frequent exchange of second-hand furnishings among homes, and increasing resistance of bedbugs to pesticides.

Numerous technologies have been developed to control bedbugs. For example, pesticides exemplified by pyrethroids and organophosphates, have been used to kill bedbugs. However, bedbugs can develop resistance to such pesticides and higher dosages and/or the use of other pesticides may be required for effective control. Furthermore, there is growing resistance by consumers to use pesticides in their homes. Another solution is the use of dry ice and/or liquid nitrogen, or the application of heat, to treat spaces and articles infested by bedbugs. However, these treatments cannot fully infiltrate areas of harbourage in the treatment areas enabling some bedbugs to survive the treatment, and then, subsequently re-infest the spaces and articles. Other treatment methods include physical removal of bedbugs by vacuuming or the use of physical traps. Yet other treatments are exemplified by the application of desiccant dusts and the like. In many cases, however, bedbugs avoid contact with the dusts by remaining in areas of harbourage for extended periods of time.

(E)-4-oxo-hex-2-enal and (E)-4-oxo-oct-2-enal have been reported as anti-aphrodisiac defense semiochemical signals, released by juvenile bedbugs. The similarity in response from the two substances suggests that the receptor binding may not be very specific for the part of molecules from carbon 5 and upward.

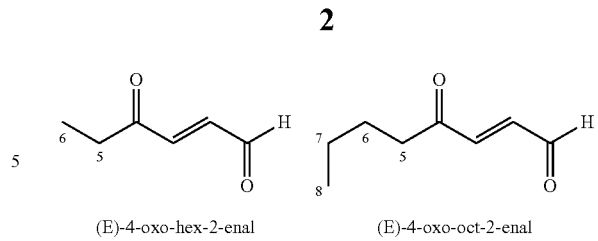

(E)-4-oxo-hex-2-enal     (E)-4-oxo-oct-2-enal

In separate studies, (E)-hex-2-enal and (E)-oct-2-enal have been reported function as alarm and/or aggregation signals. The findings could suggest that the chemical binding from the part of molecules from carbons 5 and upward may not be as important as the unsaturated aldehyde moiety (carbons 1-4), in producing the aggregation and/or alarm signal.

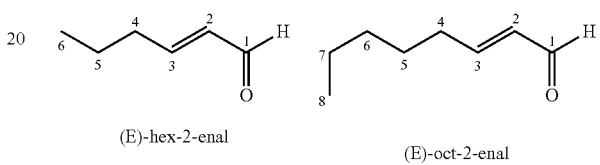

(E)-hex-2-enal     (E)-oct-2-enal

U.S. Pat. No. 7,288,573 describes methods of repelling insects, specifically mosquitoes, ticks and cockroaches, using compounds having the general formula:

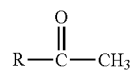

in which R is C4-C20 linear or branched alkyl, preferably linear and preferably C7-C20 alkyl.

U.S. Pat. No. 7,892,528 and U.S. Patent Application Publication No. 2011/0099886 describe methods for attracting and thereby controlling bedbugs by volatizing synthetic pheromones and generating infrared heat and exposing bedbugs thereto. Formulations comprising the synthetic pheromones are described as including a monoterpene, a saturated aldehyde, an unsaturated aldehyde, a ketone and preferably an acetate. Most preferred are formulations comprising nonanal, decanal, (E)-2-hexanal, (E)-2-octenal, (E,E)-2,4-octadienal, benzaldehyde, benzyl alcohol, (+)-limonene, (−)-limonene and sulcatone.

U.S. Patent Application Publication No. 2011/0289824 describes compounds, methods and devices for detecting and/or treating insect infestations, including bedbugs. The compounds have an oxime, hydrazone, amidine, imino or imine functional group and act as insect attractant, aggregating or arresting compounds. The compounds may be combined with an insecticide or pheromone.

International Patent Application Publication No. WO2010/126576 and U.S. Patent Application Publication No. 2012/0046359 describe methods for controlling or repelling bedbugs using formulations comprising at least one alkyl ketone or cyclic ketone compound. The alkyl ketone or cyclic ketone compound contain a total number of carbon atoms between 10 and 16 carbon atoms, and preferably between 12 and 16 or 13 and 16 carbon atoms.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a control and repellant for *Cimicidae* populations. In accordance with one aspect of the invention, there is provided a composition for repelling bedbugs comprising a carrier and one or more compounds of general formula (I), or a pro-form or intermediate thereof:

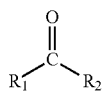

wherein: $R_1$ is selected from the group consisting of: H, hydroxy, $C_1$-$C_4$ alkyl and alkoxy, and $R_2$ is selected from the group consisting of: $C_1$-$C_4$ acyl, $C_1$-$C_6$ alkyl, $C_2$-$C_9$ alkenyl; $C_2$-$C_4$ alkynyl, alkoxy, furyl and —$NR_3R_4$, wherein $R_3$ and $R_4$ are independently selected from the group consisting of: H, $C_1$-$C_4$ alkyl, $C_2$-$C_4$ alkenyl and —$CH_2C(OCH_3)_2$, and wherein:

each $C_1$-$C_6$ alkyl is optionally substituted with one or more substituents independently selected from the group consisting of: hydroxy, $C_1$-$C_4$ acyl, $C_1$-$C_4$ alkyl, alkoxy, carbonyl, carboxy and —$NR_5R_6$, wherein $R_5$ and $R_6$ are independently $C_1$-$C_4$ alkyl or alkoxy, each $C_2$-$C_9$ alkenyl is optionally substituted with one or more substituents independently selected from the group consisting of: $C_1$-$C_4$ acyl, $C_1$-$C_4$ alkyl, carbonyl, carboxy, hydroxy and furyl, each $C_2$-$C_4$ alkynyl is optionally substituted with one or more substituents independently selected from the group consisting of: $C_1$-$C_4$ acyl, $C_1$-$C_4$ alkyl, alkoxy, carboxy, hydroxy and furyl, and each alkoxy is optionally substituted with one or more substituents independently selected from the group consisting of: carbonyl, carboxy, furyl, and tetrahydrofuryl; and wherein the one or more compounds have bedbug repellent activity.

In accordance with another aspect, there is provided a kit for repelling bedbugs comprising the composition of the invention, and instructions for use.

In accordance with another aspect, there is provided a use of a composition of the invention for repelling bedbugs.

In accordance with another aspect, there is provided a method for repelling bedbugs comprising applying to an area known or suspected of containing bedbugs a composition of the invention.

In accordance with another aspect, there is provided a method of preventing bedbug colonization comprising applying to an area prone to bedbug colonization or capable of harbouring bedbugs a composition of the invention.

In accordance with another aspect, there is provided a method for repelling bedbugs, comprising contacting the bedbugs with a composition of the invention or vapour therefrom.

BRIEF DESCRIPTION OF THE DRAWINGS

These and other features of the invention will become more apparent in the following detailed description in which reference is made to the appended drawing.

The FIGURE presents (A) a bar graph showing the ability of exemplary compounds of the invention to repel bedbugs (% repellency) at a concentration of 25% w/w in hexane soaked onto a slow-release bead. Values shown are the average repellency shown over 3 periods (1 hour, 24 hours and 48 hours), and (B) a chart showing the % repellency for each compound. STI-101-002 is 4-oxo2-hexenal; STI-101-004 is 4-oxo-2-octenal; and STI-101-088 is the known bedbug repellent phenethyl propionate.

DETAILED DESCRIPTION OF THE INVENTION

The present invention relates to compositions having bedbug repellent activity and methods for controlling and/or repelling bedbugs. The compositions of the invention are useful, for example, for eradication of established bedbug colony infestations and/or for prophylactic application to prevent establishment of bedbug colonies. It is within the scope of the present invention to control, detect and/or repel bedbugs by combining the compositions with other treatments exemplified by infrared irradiation, production of sonic airwaves, and the like.

Accordingly, the present invention provides for compositions comprising one or more compounds having bedbug repellant activity. In certain exemplary embodiments, the compounds may be, for example, naturally occurring semiochemicals or analogs of naturally occurring semiochemicals, wherein such analogs include structural analogs as well as functional analogs (i.e. compounds with only minimal structural similarity, but which exhibit one or more desirable activities of a naturally occurring semiochemical, including, but not limited to, bedbug repellent activity).

In some embodiments, the compositions comprise one or more compounds of general formula (I), as described in more detail below. The compositions can be formulated in various formats, for example, as desiccant dusts which comprise suitable particulate and/or powdered carriers, as liquids, fluids, solutions, gels or suspensions, which in certain embodiments may be mixed with or applied to suitable carriers and/or matrices.

Definitions

Unless defined otherwise, all technical and scientific terms used herein have the same meaning as commonly understood by one of ordinary skill in the art to which this invention belongs.

As used herein, the term "about" refers to an approximately +/−10% variation from a given value. It is to be understood that such a variation is always included in any given value provided herein, whether or not it is specifically referred to.

The term "bedbug repellent activity," as used herein with reference to a compound or composition means that the compound or composition, when tested in a bioassay such as those described in the Examples provided herein, exhibits a minimal % repellency of 50% in at least one assay.

The term "$C_1$-$C_4$ acyl," as used herein refers to the group —C(O)R, where R is hydrogen, $C_1$-$C_4$ alkyl or substituted $C_1$-$C_4$ alkyl.

The term "$C_1$-$C_6$ alkyl," as used herein, refers to a straight chain or branched hydrocarbon of one to six carbon atoms, wherein the alkyl may optionally be substituted as described herein.

The term "$C_2$-$C_9$ alkenyl," as used herein, refers to a straight chain or branched hydrocarbon of two to seven carbon atoms having one or more carbon to carbon double bond, wherein the alkenyl may optionally be substituted as described herein.

The term "$C_2$-$C_4$ alkynyl," as used herein, refers to a straight chain or branched hydrocarbon of two to four carbon atoms having one or more carbon to carbon triple bond, wherein the alkynyl may optionally be substituted as described herein.

The term "alkoxy," as used herein, refers to the group —OR, where R is $C_1$-$C_4$ alkyl, wherein the alkoxy may optionally be substituted as described herein.

The term "carbonyl," as used herein, refers to the group =O.

The term "carboxy," as used herein, refers to the group —C(O)OR, where R is $C_1$-$C_4$ alkyl or substituted $C_1$-$C_4$ alkyl.

The term "plurality" as used herein means more than one, for example, two or more, three or more, four or more, and the like.

"Naturally occurring," as used herein, as applied to an object, refers to the fact that an object can be found in nature. For example, a compound that can be isolated from a source in nature and which has not been intentionally modified by man in the laboratory is naturally occurring.

Compounds

The compounds for inclusion in the compositions of the invention are compounds having bedbug repellant activity. Such compounds may be, for example, naturally occurring semiochemicals, or structural and/or functional analogs of naturally occurring semiochemicals.

In certain embodiments, one or more of the compounds for inclusion in the compositions is a compound of general formula (I), or a pro-form or intermediate thereof:

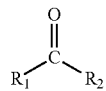

(I)

wherein:

$R_1$ is selected from the group consisting of: H, hydroxy, $C_1$-$C_4$ alkyl and alkoxy, and $R_2$ is selected from the group consisting of: $C_1$-$C_4$ acyl, $C_1$-$C_6$ alkyl, $C_2$-$C_9$ alkenyl; $C_2$-$C_4$ alkynyl, alkoxy, furyl and —NR$_3$R$_4$, wherein $R_3$ and $R_4$ are independently selected from the group consisting of: H, $C_1$-$C_4$ alkyl, $C_2$-$C_4$ alkenyl and —CH$_2$C(OCH$_3$)$_2$, and wherein:

each $C_1$-$C_6$ alkyl is optionally substituted with one or more substituents independently selected from the group consisting of: hydroxy, $C_1$-$C_4$ acyl, $C_1$-$C_4$ alkyl, alkoxy, carbonyl, carboxy and —NR$_5$R$_6$, wherein $R_5$ and $R_6$ are independently $C_1$-$C_4$ alkyl or alkoxy, each $C_2$-$C_9$ alkenyl is optionally substituted with one or more substituents independently selected from the group consisting of: $C_1$-$C_4$ acyl, $C_1$-$C_4$ alkyl, carbonyl, carboxy, hydroxy and furyl, each $C_2$-$C_4$ alkynyl is optionally substituted with one or more substituents independently selected from the group consisting of: $C_1$-$C_4$ acyl, $C_1$-$C_4$ alkyl, alkoxy, carboxy, hydroxy and furyl, and each alkoxy is optionally substituted with one or more substituents independently selected from the group consisting of: carbonyl, carboxy, furyl, and tetrahydrofuryl.

In some embodiments, one or more of the compounds for inclusion in the compositions is a compound of general formula (I) with the proviso that the compound is other than geranylacetone (6,10-dimethyl-5,9-undecadien-2-one), pseudoionone (6,10-dimethyl-3,5,9-undecatrien-2-one) or 3-decen-2-one.

In some embodiments, one or more of the compounds for inclusion in the compositions is a compound of general formula (I) with the proviso that when $R_2$ is $C_4$-$C_6$ alkyl, $R_1$ is other than methyl.

In some embodiments, one or more of the compounds for inclusion in the compositions is a compound of general formula (I) with the proviso that when $R_1$ is $C_1$-$C_4$ alkyl and $R_2$ is $C_1$-$C_6$ alkyl or $C_2$-$C_9$ alkenyl, the longest carbon chain in the compound is less than 10 carbon atoms in length.

In some embodiments, one or more of the compounds for inclusion in the compositions is a compound of general formula (I) with the proviso that when $R_1$ is $C_1$-$C_4$ alkyl and $R_2$ is $C_1$-$C_6$ alkyl or $C_2$-$C_9$ alkenyl, the total number of carbon atoms in the compound is less than 10.

In some embodiments, one or more of the compounds for inclusion in the compositions is a compound of general formula (I) as described above, wherein each $C_2$-$C_4$ alkynyl is optionally substituted with one or more alkoxy groups.

In some embodiments, one or more of the compounds for inclusion in the compositions is a compound of general formula (I) in which $R_2$ is:

(i) a substituent of general formula (II):

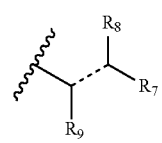

(II)

wherein - - - represents a double or triple bond, $R_7$ is selected from the group consisting of: H, $C_1$-$C_5$ alkyl, $C_1$-$C_5$ acyl, carboxy, furyl and tetrahydrofuryl; $R_8$ is absent or $R_8$ is H or $C_1$-$C_4$ alkyl, and $R_9$ is H or $C_1$-$C_4$ alkyl, wherein the $C_1$-$C_5$ alkyl is optionally substituted with one or more substituents selected from the group consisting of: $C_1$-$C_4$ alkyl, alkoxy and hydroxy:

or (ii) a substituent of general formula (III):

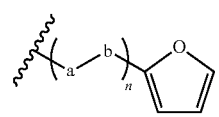

(III)

wherein a is —O— and b is CH$_2$, or a-b represents —CHR'=CHR"—, wherein R' and R" are each independently H or $C_1$-$C_4$ alkyl, and n=0 or 1;

or (iii) selected from the group consisting of: —NR$_{10}$R$_{11}$, $C_1$-$C_6$ alkyl and $C_2$-$C_9$ alkenyl, wherein $R_{10}$ is H or $C_1$-$C_4$ alkyl, and $R_{11}$ is $C_1$-$C_4$ alkyl or $C_2$-$C_4$ alkenyl, and wherein the $C_1$-$C_6$ alkyl is optionally substituted with one or more substituents selected from the group consisting of: hydroxy, alkoxy, $C_1$-$C_4$ alkyl, $C_1$-$C_4$ acyl, carboxy, carbonyl and —NR$_5$R$_6$, wherein $R_5$ and $R_6$ are independently $C_1$-$C_4$ alkyl or alkoxy; and the $C_2$-$C_9$ alkenyl is optionally substituted with one or more substituents selected from the group consisting of: hydroxy, $C_1$-$C_4$ alkyl, $C_1$-$C_4$ acyl, carboxy and carbonyl;

or (iv) selected from the group consisting of:

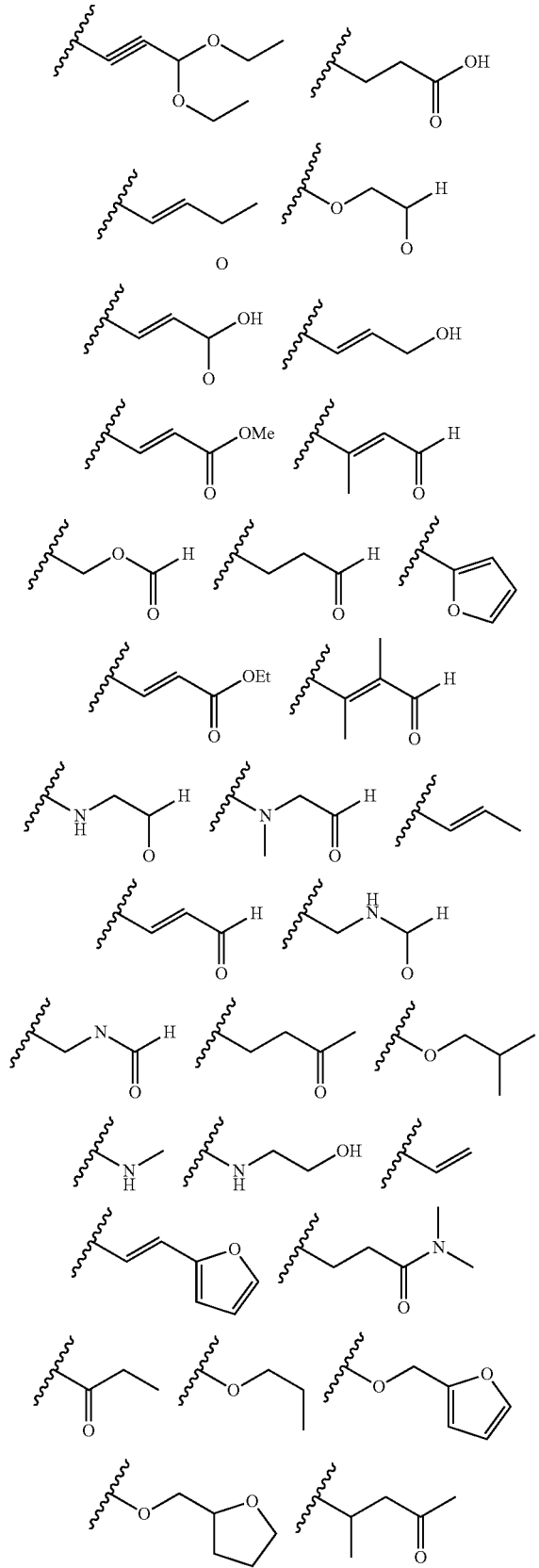

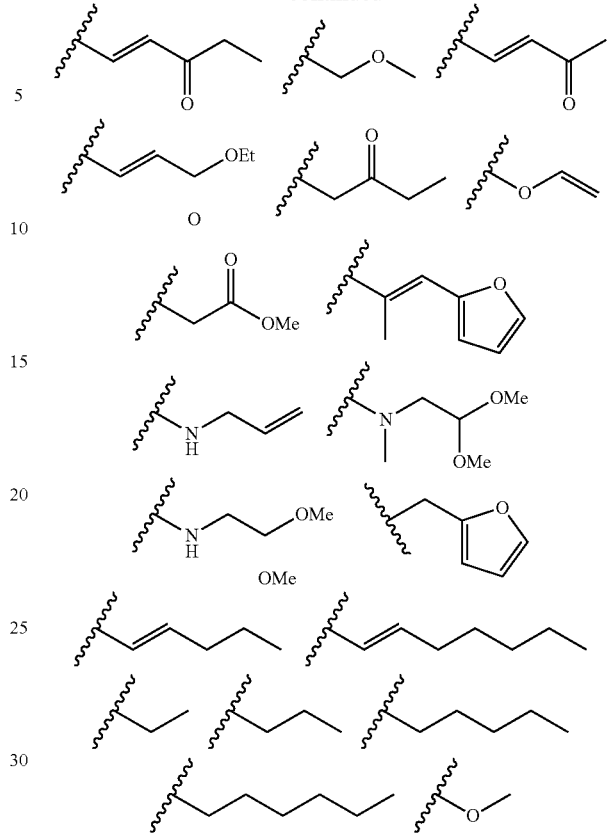

In some embodiments, one or more of the compounds for inclusion in the compositions is a compound of general formula (I) in which $R_1$ is $C_1$-$C_4$ alkyl or alkoxy, and $R_2$ is:
(i) a substituent of general formula (II):

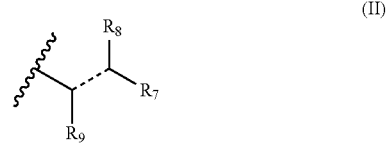

(II)

wherein - - - represents a double or triple bond, $R_7$ is selected from the group consisting of: $C_1$-$C_5$ alkyl, $C_1$-$C_5$ acyl, carboxy and furyl; $R_8$ is absent or $R_8$ is H or $C_1$-$C_4$ alkyl, and $R_9$ is H or $C_1$-$C_4$ alkyl, wherein the $C_1$-$C_5$ alkyl is optionally substituted with one or more substituents selected from the group consisting of: alkoxy and hydroxy:
or (ii) a substituent of general formula (III):

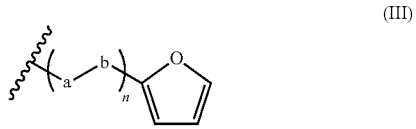

(III)

wherein a is —O— and b is $CH_2$, or a-b represents —CHR'=CHR"—, wherein R' is H or $C_1$-$C_4$ alkyl and R" is H, and n=0 or 1;
or (iii) selected from the group consisting of: $C_1$-$C_6$ alkyl and $C_2$-$C_9$ alkenyl, wherein the $C_1$-$C_6$ alkyl is optionally substituted with one or more substituents selected from the group consisting of: $C_1$-$C_4$ alkyl and carbonyl, the $C_2$-$C_9$ alkenyl is optionally substituted with one or more $C_1$-$C_4$ alkyl.

In certain embodiments, one or more of the compounds for inclusion in the compositions is a compound of general formula (I), wherein $R_1$ is selected from the group consisting of: H, $C_1$-$C_4$ alkyl and alkoxy, and $R_2$ is a substituent of general formula (II) as described under point (i) above.

In certain embodiments, one or more of the compounds for inclusion in the compositions is a compound of general formula (I), wherein $R_1$ is $C_1$-$C_4$ alkyl or alkoxy, and $R_2$ is a substituent of general formula (III) as described under point (ii) above.

In certain embodiments, one or more of the compounds for inclusion in the compositions is a compound of general formula (I), wherein $R_2$ is a substituent of general formula (III) as described under point (ii) above and a-b represents —CHR'=CHR"—, wherein R' is H or $C_1$-$C_4$ alkyl and R" is H.

In certain embodiments, one or more of the compounds for inclusion in the compositions is a compound of general formula (I), wherein $R_1$ is H or $C_1$-$C_4$ alkyl, and $R_2$ is selected from the group consisting of: —$NR_{10}R_{11}$, $C_1$-$C_6$ alkyl and $C_2$-$C_9$ alkenyl, as described under point (iii) above.

In certain embodiments, one or more of the compounds for inclusion in the compositions is an intermediate formed during synthesis of a compound of general formula (I) and having general formula (IV):

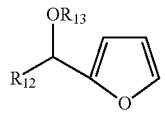

(IV)

wherein: $R_{12}$ is $C_1$-$C_4$ alkyl or $C_2$-$C_4$ alkenyl, and $R_{13}$ is H, $C_1$-$C_4$ alkyl or a protecting group, and wherein each $C_1$-$C_4$ alkyl is optionally substituted with one or more substituents independently selected from the group consisting of: hydroxy, $C_1$-$C_4$ acyl, $C_1$-$C_4$ alkyl, alkoxy, carbonyl, carboxy and $NR_5R_6$, wherein $R_5$ and $R_6$ are independently selected from the group consisting of: H, $C_1$-$C_4$ alkyl and alkoxy.

In certain embodiments, one or more of the compounds for inclusion in the compositions is an intermediate formed during synthesis of a compound of general formula (I) and having general formula (IV), as described above, wherein $R_{13}$ is H or a protecting group.

In certain embodiments, one or more of the compounds for inclusion in the compositions is an intermediate formed during synthesis of a compound of general formula (I) and having general formula (IV), as described above, wherein each $C_1$-$C_4$ alkyl is optionally substituted with one or more substituents independently selected from the group consisting of: hydroxy, $C_1$-$C_4$ alkyl and alkoxy.

In certain embodiments, one or more of the compounds for inclusion in the compositions is an intermediate formed during synthesis of a compound of general formula (I) and having general formula (IV), as described above, wherein each $C_1$-$C_4$ alkyl is optionally substituted with one or more $C_1$-$C_4$ alkyl groups.

In certain embodiments, one or more of the compounds for inclusion in the compositions is a compound of general formula (I) in which $R_1$ is selected from the group consisting of: H, an alkyl group such as —$CH_3$, —$CH(CH_3)_2$, —$CH_2CH_3$, —$CH_2CH_2CH_3$, —$CH_2CH(CH_3)_2$, —$CH_2CH_2CH_2CH_3$, —$CH(CH_3)CH_2CH_3$, —$CH(CH_2CH_3)_2$, —$CH(CH_3)CH_2CH_2CH_3$, —$CH_2CH(CH_3)CH_2CH_3$, —$CH_2CH_2CH_2CH(CH_3)_2$, —$CH_2CH_2CH_2CH_2CH_3$, —$CH_2CH_2CH_2CH_2CH_2CH_3$, $CH_2CH_2CH_2CH_2CH_2CH_2CH_3$, hydroxy, an alkoxy group such as —$OCH_3$, —$OCH_2CH_3$, —$OCH(CH_3)_2$, —$OCH_2CH_2CH_3$, —$OCH_2CH(CH_3)_2$, —$OCH_2CH_2CH_2CH_3$, —$OCH(CH_3)CH_2CH_3$, —$OCH(CH_2CH_3)_2$, —$OCH(CH_3)CH_2CH_2CH_3$, —$OCH_2CH(CH_3)CH_2CH_3$, —$OCH_2CH_2CH_2CH(CH_3)_2$, —$OCH_2CH_2CH_2CH_2CH_3$, —$OCH_2CH_2CH_2CH_2CH_2CH_3$, —$OCH_2CH_2CH_2CH_2CH_2CH_2CH_3$, and an amino group, such as —$NH_2$, —$NHCH_3$, —$N(CH_3)_2$, —$NHCH_2CH_3$, —$NHCH(CH_3)_2$, —$NHCH_2CH_2CH_3$, —$NHCH_2CH(CH_3)_2$, —$NHCH_2CH_2CH_2CH_3$, —$NHCH(CH_3)CH_2CH_3$, —$NHCH(CH_2CH_3)_2$, —$NHCH(CH_3)CH_2CH_2CH_3$, —$NHCH_2CH(CH_3)CH_2CH_3$, —$NHCH_2CH_2CH(CH_3)_2$, —$NHCH_2CH_2CH_2CH_2CH_3$, —$NHCH_2CH_2CH_2CH_2CH_2CH_3$, —$NHCH_2CH_2CH_2CH_2CH_2CH_2CH_3$, and $R_2$ is selected from the group consisting of:

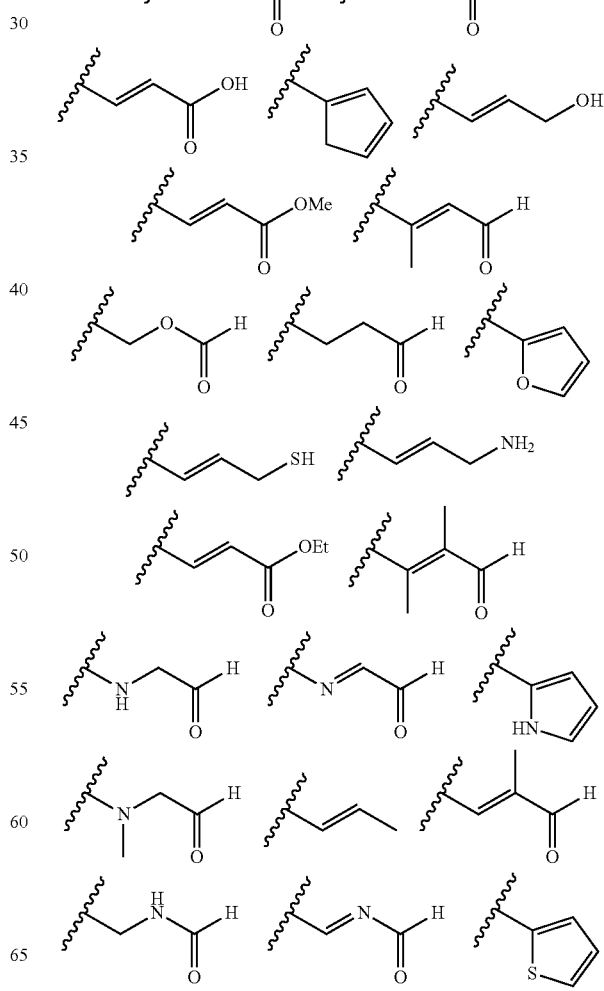

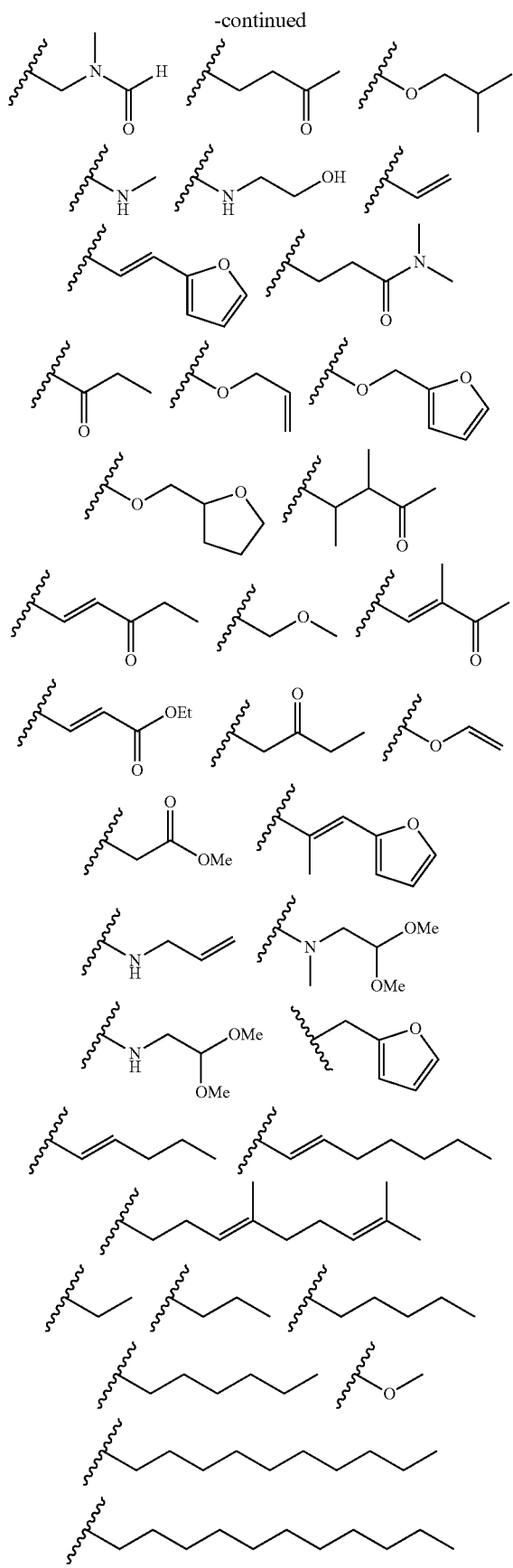

In certain embodiments, one or more of the compounds for inclusion in the compositions is a compound of general formula (I) in which $R_1$ is selected from the group consisting of: H, an alkyl group such as $-CH_3$, $-CH(CH_3)_2$, $-CH_2CH_3$, $-CH_2CH_2CH_3$, $-CH_2CH(CH_3)_2$, $-CH_2CH_2CH_2CH_3$, $-CH(CH_3)CH_2CH_3$, hydroxy, and an alkoxy group such as $-OCH_3$, $-OCH_2CH_3$, $-OCH(CH_3)_2$, $-OCH_2CH_2CH_3$, $-OCH_2CH(CH_3)_2$, $-OCH_2CH_2CH_2CH_3$, $-OCH(CH_3)CH_2CH_3$, and $R_2$ is selected from the group consisting of:

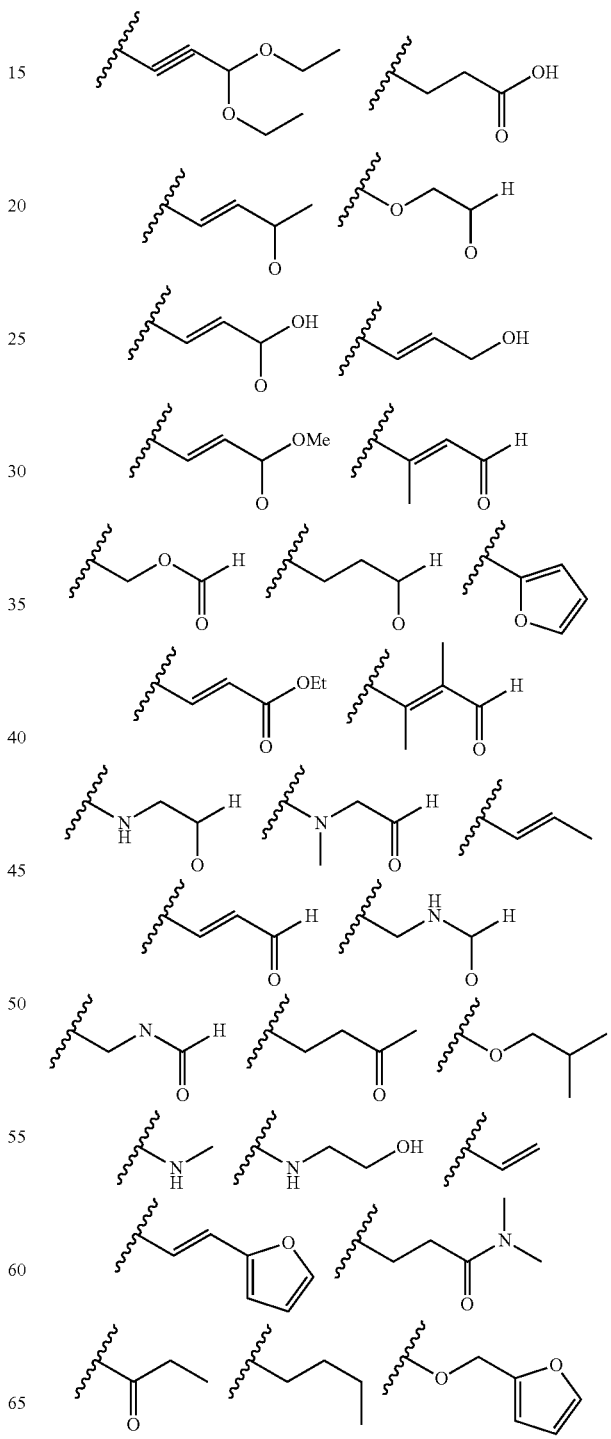

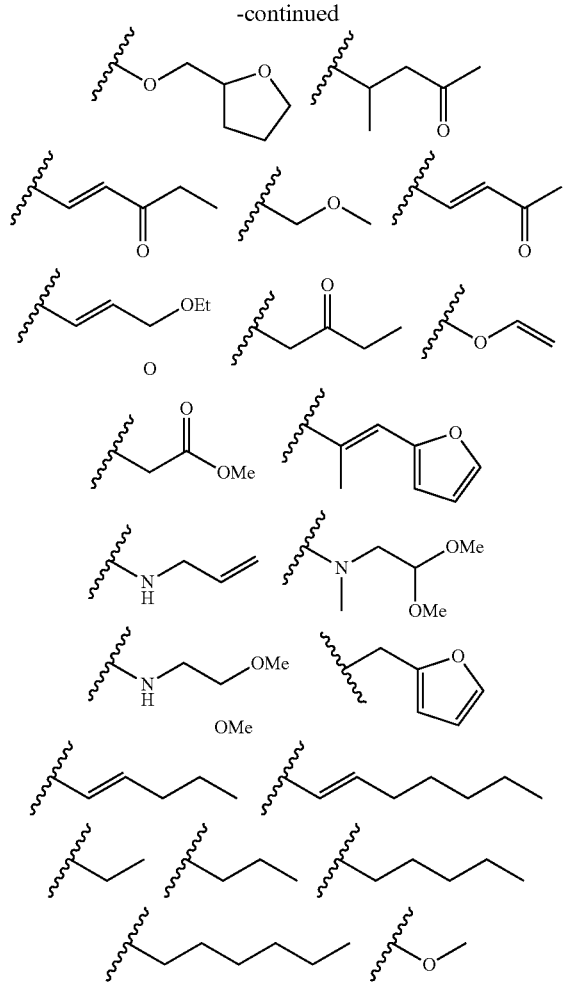

In certain embodiments, one or more of the compounds for inclusion in the compositions is a compound of general formula (V), or a pro-form or intermediate thereof:

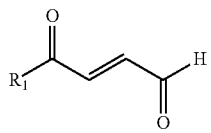

(V)

wherein $R_1$ is H or an alkyl group, for example —$CH_3$, —$CH(CH_3)_2$, —$CH_2CH_2CH_3$, —$CH_2CH(CH_3)_2$, —$CH(CH_3)CH_2CH_3$, —$CH(CH_2CH_3)_2$, —$CH(CH_3)CH_2CH_2CH_3$, —$CH_2CH(CH_3)CH_2CH_3$, —$CH_2CH_2CH_2CH(CH_3)_2$, —$CH_2CH_2CH_2CH_2CH_3$, —$CH_2CH_2CH_2CH_2CH_2CH_3$, $CH_2CH_2CH_2CH_2CH_2CH_2CH_3$;

or wherein $R_1$ is hydroxy or an alkoxy group, for example —$OCH_3$, —$OCH_2CH_3$, —$OCH(CH_3)_2$, —$OCH_2CH_2CH_3$, —$OCH_2CH(CH_3)_2$, —$OCH_2CH_2CH_2CH_3$, —$OCH(CH_3)CH_2CH_3$, —$OCH(CH_2CH_3)_2$, —$OCH(CH_3)CH_2CH_2CH_3$, —$OCH_2CH(CH_3)CH_2CH_3$, —$OCH_2CH_2CH_2CH(CH_3)_2$, —$OCH_2CH_2CH_2CH_2CH_3$, —$OCH_2CH_2CH_2CH_2CH_2CH_3$, —$OCH_2CH_2CH_2CH_2CH_2CH_2CH_3$;

or wherein $R_1$ is an amino group, for example —$NH_2$, —$NHCH_3$, —$N(CH_3)_2$, —$NHCH_2CH_3$, —$NHCH(CH_3)_2$, —$NHCH_2CH_2CH_3$, —$NHCH(CH_3)_2$, —$NHCH_2CH_2CH_2CH_3$, —$NHCH(CH_3)CH_2CH_3$, —$NHCH(CH_2CH_3)_2$, —$NHCH(CH_3)CH_2CH_2CH_3$, —$NHCH_2CH(CH_3)CH_2CH_3$, —$NHCH_2CH_2CH_2CH(CH_3)_2$, —$NHCH_2CH_2CH_2CH_2CH_3$, —$NHCH_2CH_2CH_2CH_2CH_2CH_3$, —$NHCH_2CH_2CH_2CH_2CH_2CH_2CH_3$.

In certain embodiments, one or more of the compounds for inclusion in the compositions is a compound of general formula (V), wherein $R_1$ is H; an alkyl group selected from the group consisting of: —$CH_3$, —$CH(CH_3)_2$, —$CH_2CH_2CH_3$, —$CH_2CH(CH_3)_2$, —$CH(CH_3)CH_2CH_3$; hydroxy; or an alkoxy group selected from the group consisting of: —$OCH_3$, —$OCH_2CH_3$, —$OCH(CH_3)_2$, —$OCH_2CH_2CH_3$, —$OCH_2CH(CH_3)_2$, —$OCH_2CH_2CH_2CH_3$, —$OCH(CH_3)CH_2CH_3$.

In some embodiments, the compositions comprise mixtures of two or more of (E)-4-oxo-hex-2-enal, (E)-4-oxo-oct-2-enal, (E)-hex-2-enal, and (E)-oct-2-enal. In some embodiments, the compositions may comprise mixtures provided with: (i) one of (E)-4-oxo-hex-2-enal, (E)-4-oxo-oct-2-enal, (E)-hex-2-enal or (E)-oct-2-enal, plus (ii) one or more analogs of (E)-4-oxo-hex-2-enal, (E)-4-oxo-oct-2-enal, (E)-hex-2-enal or (E)-oct-2-enal. In some embodiments, the compositions may comprise one or more analogs of (E)-4-oxo-hex-2-enal, (E)-4-oxo-oct-2-enal, (E)-hex-2-enal and (E)-oct-2-enal. In certain embodiments, such analogs of (E)-4-oxo-hex-2-enal, (E)-4-oxo-oct-2-enal, (E)-hex-2-enal and (E)-oct-2-enal fall within the scope of general formula (I) above.

In certain embodiments, one or more of the compounds for inclusion in the compositions is a compound selected from the group consisting of:

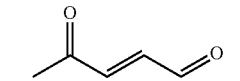

1

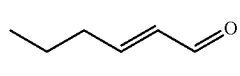

38

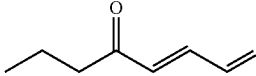

3

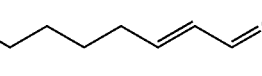

39

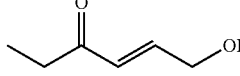

6

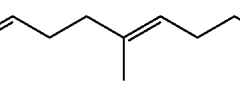

44

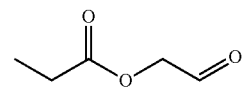

8

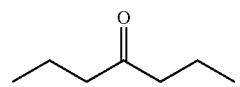

51

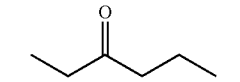

26

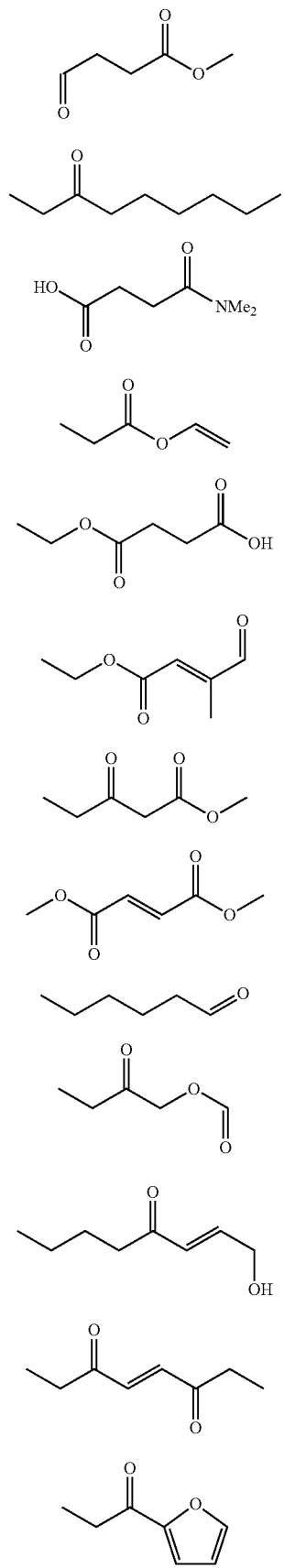
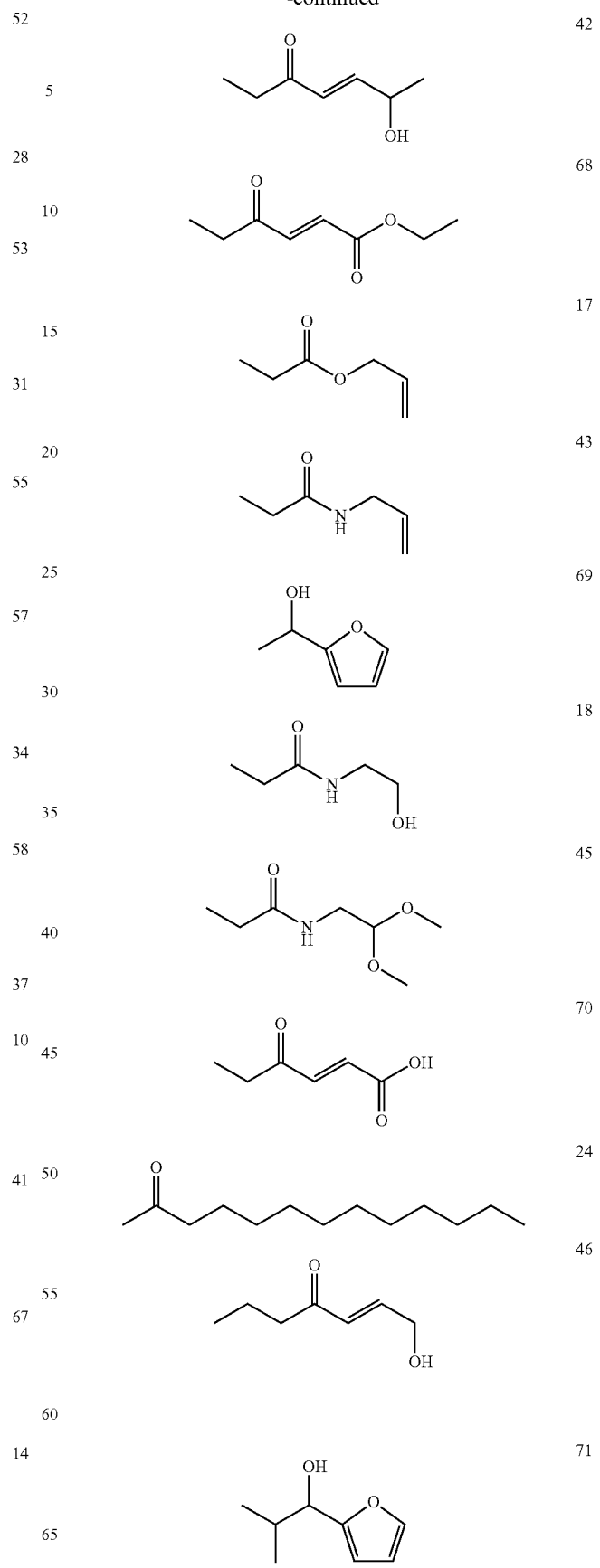

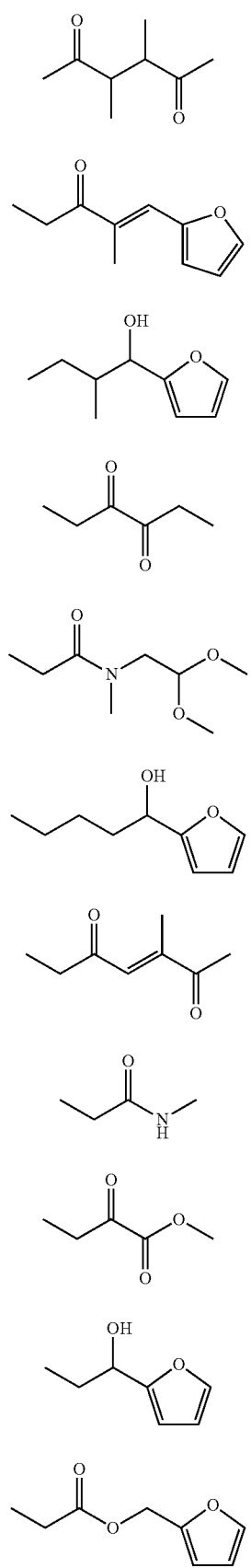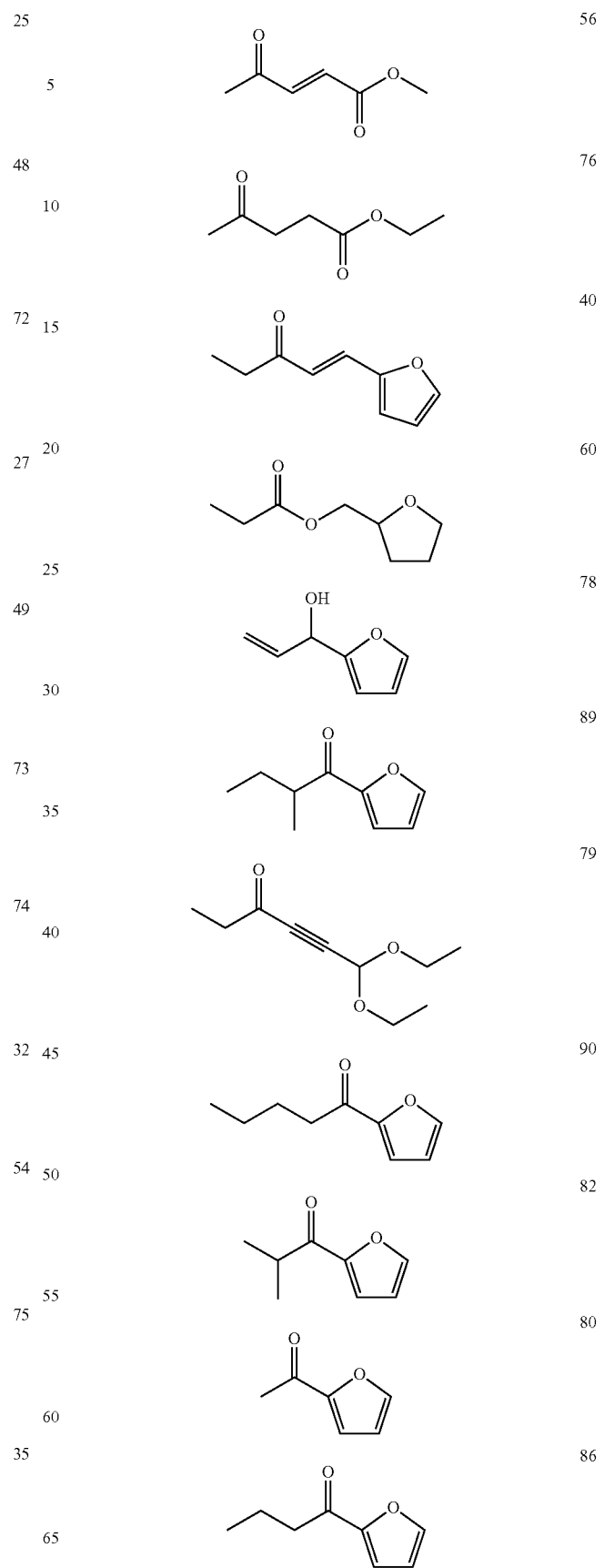

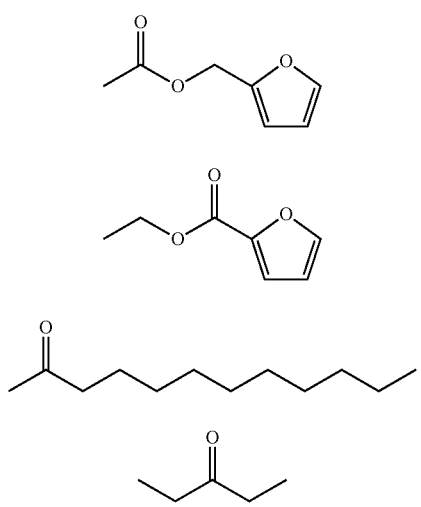
In certain embodiments, one or more of the compounds for inclusion in the compositions is a compound selected from the group of compounds shown in Table 2.
In certain embodiments, one or more of the compounds for inclusion in the compositions is a compound selected from the group consisting of:
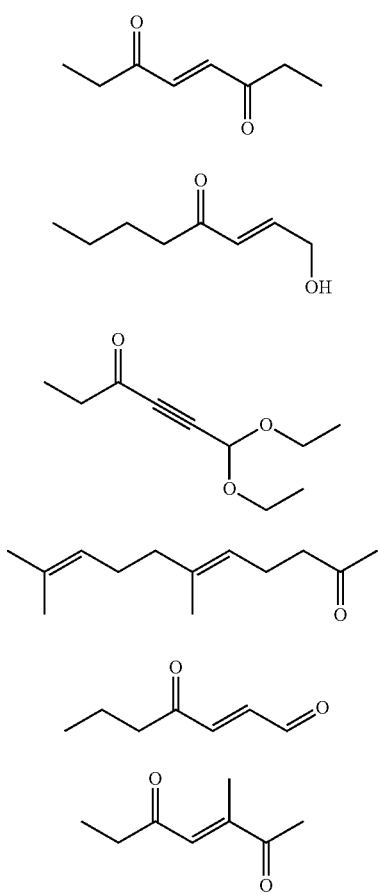
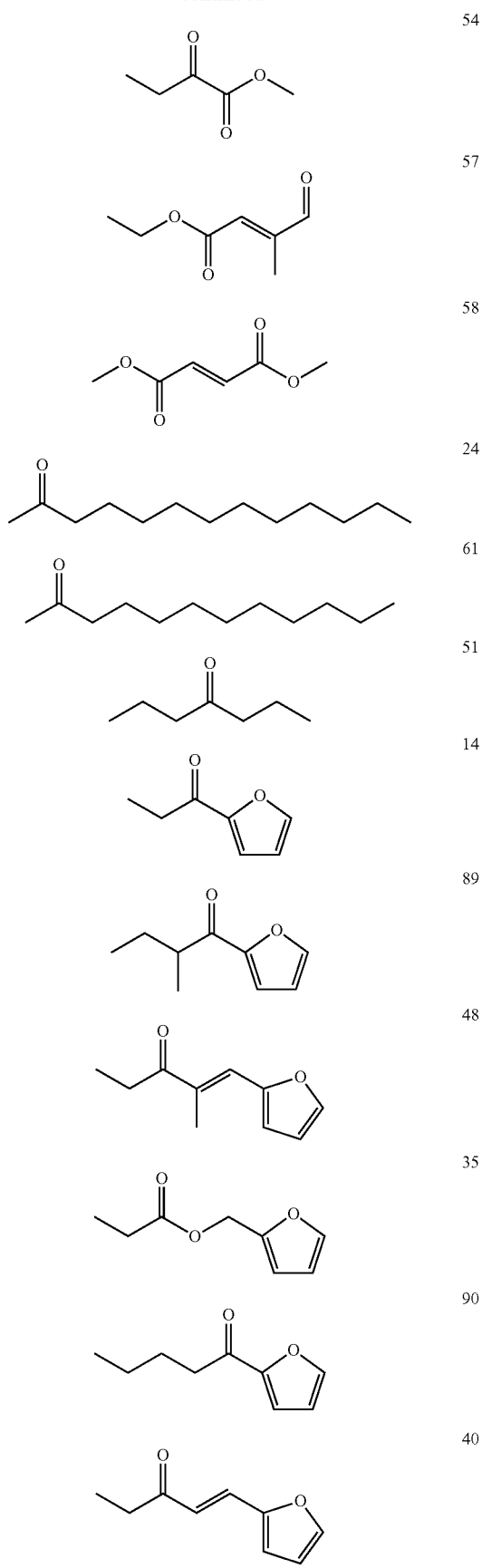

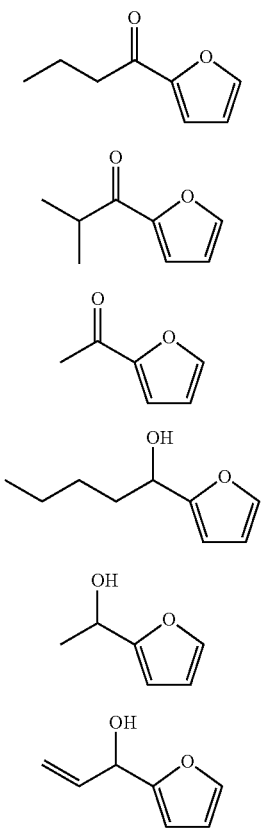

Certain compounds of Formula (I) may have one or more asymmetric (chiral) centres and/or one or more unsaturated bonds. As a consequence, these compounds can be present as racemates, individual enantiomers, mixtures of enantiomers, individual diastereomers, mixtures of diastereomers, individual isomers and mixtures of isomers. Certain embodiments of the invention provide for the inclusion of such compounds in the compositions in an enantiomeric, diastereomeric or isomeric form, or as mixtures of enantiomers, diastereomers or isomers.

Also contemplated in certain embodiments of the invention are various salts of the compounds of Formula (I). One skilled in the art will appreciate that certain compounds of Formula (I) can possess sufficiently acidic, a sufficiently basic, or both functional groups, and accordingly react with a number of organic or inorganic bases, or organic or inorganic acids, to form salts. Generally, any salts included in the compositions would be non-toxic to humans and household animals. One skilled in the art will understand that the particular counter ion forming a part of such a salt is usually not of a critical nature, so long as the salt as a whole is acceptable in terms of toxicity and compatibility with any surfaces to which it is to be applied, and as long as the counter ion does not contribute undesired qualities to the salt as a whole.

Some embodiments of the invention provide for one or more of the compounds to be included in the compositions in a precursor or "pro-form." As is known in the art, pro-forms of compounds generally include one or more functional groups that have been "masked" such that the compound is inactive until the masking group has been removed. Various groups suitable for masking common functional groups and conditions for their removal are known in the art. For example, carbonyl functionalities could be masked as ketals, acetals or hydrazones, that are convertible to the desired active compounds upon activation by mechanisms exemplified by exposure to heat, exposure to water, exposure to basic solutions, exposure to acidic solutions, exposure to ultraviolet light, and the like.

The compounds for inclusion in the compositions of the invention may be obtained from various commercial sources (for example, Sigma-Aldrich, St. Louis, Mo.), or they may be readily synthesized using conventional methods for chemical synthesis with readily available starting materials. In addition, a number of commercial companies offer custom synthesis (for example, Best West Labs, Salt Lake City, Utah; Oakwood Products, Inc., West Columbia, S.C.; and Tyger Scientific, Inc. Ewing, N.J.) and could be used as a source for the compounds.

Compositions

Exemplary compositions of the present invention comprise one or a combination of the compounds disclosed herein. The compositions typically also comprise one or more suitable carriers. Within the scope of the present invention, the term "carrier" can be used to refer to various organic or inorganic materials of natural-occurring or synthetic origin that can be used to facilitate application of the compound(s) to a locus or object to be treated. In certain embodiments, one or more carriers may be selected for providing desired stability characteristics to the compositions, for example, to enhance and/or preserve their efficacy during storage and/or transport and/or handling. Suitable carriers are exemplified by conventional pesticide dispersible carrier vehicles such as solutions, emulsions, suspensions, emulsifiable concentrates, spray powders, pastes, soluble powders, dusting agents, granules, foams, pastes, tablets, aerosols, microcapsules and the like.

In certain embodiments, the compounds are admixed with or dissolved in a suitable liquid carrier, which may be aqueous-based or non-aqueous (i.e. organic solvents), or a combination thereof. Such liquid formulations may be employed, for example, as foams, gels, emulsions, suspensions, microemulsions or emulsifiable concentrates. Liquid formulations may also be used to coat, infuse or impregnate a solid matrix, such as a polymer or wax bead or pellet, plastic, metal, cloth, paper, wood or other material.

Examples of liquid diluent carriers include, but are not limited to, inert organic solvents, such as aromatic hydrocarbons exemplified by benzene, toluene, xylene, alkyl naphthalenes; halogenated aromatic hydrocarbons; cycloalkanes exemplified by cyclohexane; paraffins exemplified by petroleum fractions and mineral oil fractions; aliphatic hydrocarbons exemplified by pentane, hexane, heptane; chlorinated aliphatic hydrocarbons exemplified by dichloromethane, methylene chloride; chloroethylenes; alcohols exemplified by methanol, ethanol, propanol, butanol, isopropyl alcohol, ethylene, and propylene glycol; ethers; esters; and the like. Other examples include oils and essential oils, such as mineral oil, wintergreen oil, neem oil, citronella oil, camphor oil, and the like.

Suitable carriers are also exemplified by aerosol propellants which are gaseous at normal temperatures and pressures, such as propane, butane, isobutene and carbon dioxide.

The compositions may further comprise one or more additional active or inactive substances. For example, in some embodiments, the compositions may include one or more of rheological agents, emulsifiers, surfactants, dispersants, polymers, excipients, binders and fragrances.

In some embodiments, the compositions comprise one or more stabilizer substances exemplified by ultra-violet radiation absorbers and/or radical scavengers such as 3-methyl-6-t-butylphenol, crotonaldehyde, N,N'-diphenyl-1,4-phenylenediamine, butylated hydroxytoluene (BHT), butylated hydroxyanisole (BHA), and/or alpha-tocopherol. In some embodiments, the compositions comprise one or more controlled-release matrix substances exemplified by starches and other polysaccharide or polymer based matrices. In certain embodiments, fragrance substances may be added to the compositions. Suitable fragrance substances are exemplified by methyl butyrate, ethyl butyrate, pentyl butyrate, linallor, citronellol, geraniol and limonene.

In certain embodiments, inclusion of one or more known insecticides, or bedbug repellents, in the compositions is contemplated. Examples of insecticides include, but are not limited to, phosphoric esters, such as acephate, chlorpyrifos, dichlorovos, malathion or propetamphos; carbamates, such as bendiocarb, carbaryl, or propoxur; pyrethroids, such as allethrin, bifenthrin, bioallethrin, bioresmethrin, cyclopro-thrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, esfenvalerate, etofenprox, fenpropathrin, fenvalerate, flumethrin, tau-fluvalinate, halfenprox, imiprothrin, permethrin, phenothrin, prallethrin, pyrethrins (pyrethrum), resmethrin, silafluofen, tefluthrin, tetramethrin or transfluthrin; nitroimines and nitromethylenes, such as 1-[(6-chloro-3-pyridinyl)-methyl]-4,5-dihydro-N-nitro-1H-imidazol-2-amine (imidacloprid), N-[(6-chloro-3-pyridyl)methyl-]$N^2$-cyano-$N^1$-methylacetamide (NI-25); phenylpyrazoles, such as fipronil or ethiprole; avermectins, such as abamectin or emamectin benzoate; spinosyns, such as spinosad or spinetoram; oxadiazines, such as indoxacarb or metaflumizone; anthranilic diamides, such as flubendiamid, chlorantraniliprole or cyantraniliprole; sulfoximines, such as sulfoxaflor; insect growth regulators, such as methoprene, chlorfluazuron, flufenoxuron, pyriproxyfen, triflumuron or flufenoxuron; and other insecticidally active compounds, such as azadirachtin, chlorfenapyr, hydramethylnon, petroleum oils or botanical oils. Examples of known bedbug repellents that may be included in the compositions, or used in conjunction with the compositions, include for example phenethyl propionate (PEP).

In some embodiments, it is contemplated that the compositions are formulated to be suitable for application to the skin and will comprise dermatologically acceptable ingredients as are known in the art and can be provided in conventional formulations suitable for topical application, such as lotions, creams, gels or sprays.

One skilled in the art will appreciate that the amount of the compound(s) to be included in the compositions will vary greatly depending on the nature of the particular formulation, and whether it is a concentrate or to be used directly. In general, each compound will be included in the composition in an amount of at least 0.0001% by weight of the composition, but may be as high as 50%, 60%, 70%, 80%, 90% or 99% by weight of the composition. In certain embodiments, ranges between about 0.01% and about 90% by weight are contemplated, for example, between about 0.1%, 0.5%, 1.0% or 2.0% and about 90% by weight, between about 0.1%, 0.5%, 1.0% or 2.0% and about 80% by weight, between about 0.1%, 0.5%, 1.0% or 2.0% and about 70% by weight, between about 0.1%, 0.5%, 1.0% or 2.0% and about 60% by weight, between about 0.1%, 0.5%, 1.0% or 2.0% and about 50% by weight, and between about 0.1%, 0.5%, 1.0% or 2.0% and about 25% by weight. In some embodiments, the compositions comprise about 1%, 2%, 3%, 4%, 5%, 6%, 7%, 8%, 9% or 10% by weight of each compound. In certain embodiments, the compositions comprise between about 15% and about 25% by weight of each compound.

As would be appreciated by the skilled worker, depending on the nature of the compound(s) and the format of the composition, it may be appropriate in certain embodiments to measure the amount of the compound(s) to include in the composition by volume. Accordingly, in some embodiments, each compound will be included in the composition in an amount of at least 0.0001% by volume of the composition, but may be as high as 50%, 60%, 70%, 80%, 90% or 99% by volume of the composition. In certain embodiments, ranges between about 0.01% and about 90% by volume are contemplated, for example, between about 0.1%, 0.5%, 1.0% or 2.0% and about 90% by volume, between about 0.1%, 0.5%, 1.0% or 2.0% and about 80% by volume, between about 0.1%, 0.5%, 1.0% or 2.0% and about 70% by volume, between about 0.1%, 0.5%, 1.0% or 2.0% and about 60% by volume, between about 0.1%, 0.5%, 1.0% or 2.0% and about 50% by volume, and between about 0.1%, 0.5%, 1.0% or 2.0% and about 25% by volume. In some embodiments, the compositions comprise about 1%, 2%, 3%, 4%, 5%, 6%, 7%, 8%, 9% or 10% by volume of each compound. In certain embodiments, the compositions comprise between about 15% and about 25% by volume of each compound.

The present invention contemplates that the compositions may be formulated and used in various forms. For example, various embodiments provide for compositions in the form of an aerosol dispenser, capsule suspension, cold fogging concentrate, dustable powder, emulsifiable concentrate, emulsion oil in water, emulsion water in oil, encapsulated granule, fine granule, granule, macrogranule, microgranule, oil dispersible powder, oil miscible flowable concentrate, oil miscible liquid, paste, smoke candle, smoke cartridge, smoke generator, smoke pellet, smoke rodlet, smoke tablet, smoke tin, soluble concentrate, soluble powder, suspension concentrate, oil dispersable or suspension in oil, tracking powder, ultra low volume (ulv) liquid, ultra low volume (ulv) suspension, vapour releasing product, water dispersible granules or tablets, water dispersible powder for slurry treatment, water soluble granules or tablets, or water soluble powder for seed treatment and wettable powder or other forms of slow release/controlled release formulations.

In certain embodiments of the invention, the compositions are provided in the form of a solid matrix that has been coated, infused or impregnated with the compounds. Examples of such matrices include various absorbent materials, paper, wood, cardboard, metal, plastic, cotton, fabric, polymer beads, and the like.

Testing

Candidate compounds or compositions comprising same can be tested for their ability to repel bedbugs by standard techniques known in the art. Exemplary techniques are described in the Examples provided herein.

Generally, the assays comprise exposing bedbugs to the compound or composition within an enclosed area, for example, a beaker, petri dish, aquarium, or other suitable chamber, and observing the movement of the bedbugs over an appropriate period of time (for example, between about 1 hour and about 72 hours). Movement away from the test compound/composition is indicative of repellent activity. Negative controls are typically solvent or other compound or composition known to have no effect on bedbugs. Positive controls may be included if desired, for example, compounds known to have bedbug repellent activity.

In accordance with certain embodiments, compounds exhibiting a minimum repellency of 50% in such an assay are selected as repellent compounds for inclusion in the compositions of the invention. In some embodiments, compounds exhibiting an average minimum repellency of 50% in at least three replicates of the assay are selected as repellent compounds for inclusion in the compositions of the invention.

One skilled in the art will appreciate that, depending on the nature of the composition in which the compound is to be included, useful compounds may be strongly repellent but with a short duration of activity, weakly repellent but with an extended duration of activity, of medium repellency with an average duration of activity, or various combinations of strength and duration. Accordingly in various embodiments, useful compounds may be those that consistently exhibit a minimum repellency of 50% over a period of 1 hour (for example, in at least three assays), those that consistently exhibit a minimum repellency of 50% over a period of 24 hours (for example, in at least three assays) or those that consistently exhibit a minimum repellency of 50% over a period of 48 hours (for example, in at least three assays).

Applications

The compositions according to the present invention can be used for control of, detecting and/or repelling bedbugs. In some embodiments, the compositions are used to control and/or repel bedbugs from *Cimex* sp. or other genera in the *Cimicidae* family, for example the genus *Haematosiphon*, or the genus *Oeciacus*. In certain embodiments, the bedbugs are from the species *Cimex lectularius, Cimex hemipterus, Leptocimex boueti, Cimex pilosellus, Cimex pipistrella*, or *Haematosiphon inodora*. In some embodiments, the bedbugs are *Cimex lectarius*.

In certain embodiments, the compositions are placed in, or applied to, an area or object suspected of containing bedbugs or prone to bedbug infestation in order to repel bedbugs therefrom.

In certain embodiments, the compositions are placed in, or applied to, an area prone to bedbug infestation or capable of harbouring bedbugs in order to prevent bedbug colonization.

Exemplary areas and objects that may be treated include, for example, beds, pillows, pillow cases, mattresses, box springs, bed frames, headboards, sheets, carpets, furniture, curtains, blinds, upholstered chairs, sofas, wood furniture, along and beneath baseboards, floor areas, under beds and/or couches, and other places bedbugs are prone to rest or hide. Areas and objects that may be treated also include objects that could act to transport bedbugs from one location to another, for example, luggage, hampers, suitcases, clothing bags, linens, clothes, and the like.

Accordingly, some exemplary uses comprise application of the compositions into and/or onto furniture, mattresses and/or box springs, drapery, flooring, junctures between flooring and walls, casings, junctures of flooring and/or walls and/or ceilings with fixtures exemplified by electrical fixtures, plumbing works, heating and/or cooling fixtures.

In some embodiments, the compositions are provided in the form of a solid matrix that has been coated, infused or impregnated with the compounds and the solid matrix is placed in an area suspected of containing bedbugs or prone to bedbug infestation, for example, a mattress, hamper, suitcase, clothing bag, linen storage closet, or other enclosure. For example, the composition could be provided as a sachet containing an absorbent material onto which the composition has been absorbed, or as beads, pellets or wooden articles onto or into which the composition has been coated or absorbed.

In certain embodiments, the composition is provided in a form similar to a dryer sheet which may be placed in an enclosure as described above, or in piles of clothes, including clean, dirty or soiled laundry, or which may be placed in the dryer in the same manner as a conventional dryer sheet.

In some embodiments, the compositions may be incorporated into various home cleaning products for use on carpets, floors, walls, closets, furniture, and the like, or in products intended for human and animal application such as lotions, powders, sprays and shampoos.

Some exemplary embodiments pertain to devices and/or apparatus for deployment and/or dispersal of the compositions of the present invention. One exemplary device comprises canisters configured for controlled delivery of the compositions in aerosol sprays. The canisters can be operable by the use of propellants, or disposable cartridges or re-usable cartridges. Another exemplary device comprises semi-permeable capsules containing the compositions therein. Another exemplary device comprises a tape and/or fabric having incorporated thereonto a composition of the present invention.

Certain embodiments pertain to use of the compositions for detection of bedbugs in indoor spaces whereby the bedbugs are repelled from their areas of harbourage to areas where they can be detected. Detection could be performed by visual observation of bedbugs outside the area of harbourage. Visual detection can be facilitated by use of physical traps to secure bedbugs. Useful physical traps are exemplified by sticky tapes, containers provided with one-way ingress ports, containers provided with liquid pesticide solutions, and the like.

Some embodiments pertain to use of the compositions for displacement of bedbugs from their areas of harbourage. Once displaced from their harbourage areas, the bedbugs could be physically removed by vacuum suction or entrapment using attractants, traps or sticky tape, or could be killed by insecticides, desiccants, heat treatments or freezing treatments, or could be allowed to find new harbourage elsewhere.

Some embodiments provide for use of the compositions for displacement of bedbugs in such ways that prevent normal reproduction cycles and colony growth. For example, the compositions could preferentially target certain members of bedbug colonies, e.g., adult males, to create imbalances in colony composition thereby affecting the ability of the colony to continue proliferation. Certain embodiments provide for the use of the compositions to confuse or disorient certain members of bedbug colonies in ways that prevent normal reproduction cycles and colony growth. For example, the compositions may impede and/or deter target members of bedbug colonies, e.g., adult males, from engaging in reproductive behaviour and thereby prevent colony proliferation.

Some embodiments pertain to an apparatus provided with a composition of the present invention. The apparatus may comprise physical traps exemplified by sticky tapes, barrier-type fabrics and the like. The apparatus may comprise containers for retaining the compositions wherein the containers are provided with one or more one-way ingress ports for bedbugs to enter into the containers after which, their egress is blocked. The apparatus may comprise containers for holding fluid compositions into which bedbugs may fall after which, their egress is prevented. The apparatus may comprise containers for retaining therein gel compositions which provide a slow, sustained release of the repellent compound(s) into the surrounding atmosphere. The apparatus may comprise containers configured for controllable discharge of the compositions as aerosols. The apparatus may comprise containers configured for controllable discharges of powdered or granular or particulate compositions.

Kits

The present invention additionally provides for kits comprising a composition of the invention for use to repel, detect and/or control bedbugs. Individual components of the kit would be packaged in separate containers and the kit may also include instructions for using the compositions to repel, detect and/or control bedbugs.

The kit may comprise the composition in one of the various forms described above, for example, in the form of an aerosol dispenser, capsule suspension, cold fogging concentrate, dustable powder, emulsifiable concentrate, emulsion oil in water, emulsion water in oil, encapsulated granule, fine granule, granule, macrogranule, microgranule, oil dispersible powder, oil miscible flowable concentrate, oil miscible liquid, paste, smoke candle, smoke cartridge, smoke generator, smoke pellet, smoke rodlet, smoke tablet, smoke tin, soluble concentrate, soluble powder, suspension concentrate, oil dispersable or suspension in oil, tracking powder, ultra low volume (ulv) liquid, ultra low volume (ulv) suspension, vapour releasing product, water dispersible granules or tablets, water dispersible powder for slurry treatment, water soluble granules or tablets, or water soluble powder for seed treatment and wettable powder or other forms of slow release/controlled release formulations.

In certain embodiments, the container for the composition will also act as a dispenser, for example, an aerosol, spray, or pump dispenser. In some embodiments, the composition may be provided in a concentrated, or solid form (for example, as a powder or granules) for reconstitution in an appropriate solvent, in which case the kit may further comprise an appropriate solvent and may also comprise one or more additional containers and/or implements to assist with mixing the components of the kit.

In some embodiments, the composition comprises a repellent compound in a pro-form that can be activated by exposure to a suitable solvent or activator, for example, an acidic or basic solvent, and the kit may optionally further comprise the solvent or activator for admixture with the compound prior to use.

In certain embodiments, the kit comprises an apparatus such as described above for use with a composition of the invention, for example, an apparatus that comprises a physical trap exemplified by sticky tapes, barrier-type fabrics and the like.

To gain a better understanding of the invention described herein, the following examples are set forth. It will be understood that these examples are intended to describe illustrative embodiments of the invention and are not intended to limit the scope of the invention in any way.

EXAMPLES

Compounds are referenced throughout the preceding description and the Examples by a designated number, which may or may not be preceded by zero(s). Thus, for example, compound 006 is also referred to, and is the same as, compound 6; compound 035 is also referred to, and is the same as, compound 35, etc.

Example 1

Repellency of Compounds of Formula (I) in Bioassays

Test Subjects:

Per individual bioassay, 10 adult or late instar nymph bed bugs, *Cimex lectularius*, of mixed sex. Bed bugs sourced from wild, field populations and tested within 2 weeks of capture. Subjects were tested one time, only.

Test Arenas:

Self-contained test arenas were of one of the following configurations:

(i) Petri Dish arenas consisted of a standard plastic, covered Petri Dish where test substrates were placed at opposite sides of the dish. Dimensions of the dish were 101.6 mm in diameter by 25.4 mm in depth.

(ii) Olfactometer consisting of a glass tube. Tube ends were plugged to prevent egress of test subjects. Test substrates were placed at opposite ends of the tube. Tube Olfactometer includes a port in the centre for introduction of test subjects. Dimensions of the tube were 15.2 mm in diameter by 304.8 mm long.

(iii) Box arenas consisted of covered plastic "Rubbermaid" box where the cover was modified to fit a mesh screen to allow movement of air between the test arena interior and outside. Test substrates were placed at opposite ends of the box arena. Dimensions of the box were 304.8 mm long by 200 mm wide by 80 mm in depth.

Test Compounds:

Compounds were either purchased from commercial sources or synthesized using conventional synthetic organic chemistry techniques (see, for example, Examples 5 to 7). Some compounds (014, 058 and 080) were tested in duplicate (one version from commercial sources and one synthesized) and the best performance is reported in the Tables below. Of the tested compounds reported in the Tables below, the following compounds were synthesized: 006, 010, 017, 018, 040, 041 to 043, 045, 046, 048, 049, 058, 067 to 075, 079, 080 to 082, 089 and 090.

Test compounds consisted of a control and treatment. The treatment consisted of a test compound mixed as a percentage w/w in a suitable solvent. The test compound solvent itself was used as a control. Solvents used were hexane, hexane:methanol, or dichloromethane:methanol.

Test Substrates:

Test substrates consisted of the following:

(i) Gauze cut to a standard size and folded upon itself to provide harbourage for test subjects.

(ii) Filter paper of standard size and folded as per (i).

(iii) Absorbent polymer "aroma" beads that were given sufficient time to fully absorb test compounds and control solvents.

Methods:

In the case of gauze and filter paper substrates, control solvents and test mixtures of known concentrations and volumes were dispensed directly onto substrates using a pipette. For polymer beads, beads were mixed w/w with solvent or test compound in a small glass jar. The jars were occasionally agitated to facilitate soaking of the beads.

Immediately after the substrates were infused with test compounds and control solvents, test subjects were introduced to the centre of the selected observation arena. Test subjects were observed at 3 or more specific time intervals, typically selected from 30 minutes, 1 hour, 3 hours, 24 hours and 48 hours after initial introduction. Only subjects that were in close contact with the treatment or control substrates were recorded. Subjects elsewhere in the arena were not included in repellency calculations. Percentage repellency was calculated based on a modification of Abbott's formula to account for negative repellency (attraction). Specifically:

$$IF(C>=T,(C-T)/C*100,(T-C)/T*-100)$$

where C is number of test subjects in contact with control substrate and T is number of test subjects in contact with treatment substrate.

Details for the testing of the individual compounds is provided in Table 1.

TABLE 1

| | Experimental Details[1, 2] | | | |
|---|---|---|---|---|
| Test Compound | Test Substrate | Compound Amount | Compound Concentration | Unit of Concentration |
| 001 | Gauze | 50 uL | 5% | w/v |
| 003 | Gauze | 50 uL | 5% | w/v |
| 006 | Gauze | 10 uL | 1% | v/v |
| 008 | Gauze | 50 uL | 5% | w/v |
| 010 | Beads | 20 uL | 25% | w/w |
| 014 | Beads | 20 uL | 25% | w/w |
| 017 | Gauze | 10 uL | 1% | v/v |
| 018 | Beads | 20 uL | 25% | w/w |
| 024 | Gauze | 50 uL | 5% | w/v |
| 025 | Beads | 20 uL | 25% | w/w |
| 026 | Gauze | 50 uL | 5% | w/v |
| 027 | Gauze | 50 uL | 5% | w/v |
| 028 | Gauze | 10 uL | 1% | v/v |
| 031 | Gauze | 50 uL | 5% | w/v |
| 032 | Beads | 20 uL | 25% | w/w |
| 034 | Gauze | 50 uL | 5% | w/v |
| 035 | Beads | 20 uL | 25% | w/w |
| 037 | Gauze | 50 uL | 5% | w/v |
| 038 | Gauze | 50 uL | 5% | w/v |
| 039 | Gauze | 50 uL | 5% | w/v |
| 040 | Gauze | 50 uL | 5% | w/v |
| 041 | Gauze | 50 uL | 5% | w/v |
| 042 | Gauze | 50 uL | 5% | w/v |
| 043 | Gauze | 50 uL | 5% | w/v |
| 044 | Gauze | 50 uL | 5% | w/v |
| 045 | Gauze | 50 uL | 5% | w/v |
| 046 | Gauze | 50 uL | 5% | w/v |
| 048 | Gauze | 50 uL | 5% | w/v |
| 049 | Gauze | 10 uL | 1% | v/v |
| 051 | Beads | 20 uL | 25% | w/w |
| 052 | Beads | 20 uL | 25% | w/w |
| 053 | Gauze | 10 uL | 1% | v/v |
| 054 | Gauze | 10 uL | 1% | v/v |
| 055 | Filter paper | 100 uL | 1% | v/v |
| 056 | Gauze | 50 uL | 5% | w/v |
| 057 | Beads | 20 uL | 25% | w/w |
| 058 | Gauze | 50 uL | 5% | w/v |

TABLE 1-continued

| | Experimental Details[1, 2] | | | |
|---|---|---|---|---|
| Test Compound | Test Substrate | Compound Amount | Compound Concentration | Unit of Concentration |
| 060 | Beads | 20 uL | 25% | w/w |
| 061 | Gauze | 50 uL | 5% | w/v |
| 062 | Gauze | 50 uL | 5% | w/v |
| 067 | Gauze | 50 uL | 5% | w/v |
| 068 | Gauze | 10 uL | 1% | v/v |
| 069 | Beads | 20 uL | 25% | w/w |
| 070 | Gauze | 10 uL | 1% | v/v |
| 071 | Gauze | 10 uL | 1% | v/v |
| 072 | Gauze | 50 uL | 5% | w/v |
| 073 | Gauze | 50 uL | 5% | w/v |
| 074 | Beads | 20 uL | 25% | w/w |
| 075 | Gauze | 10 uL | 1% | v/v |
| 076 | Gauze | 50 uL | 5% | w/v |
| 078 | Beads | 20 uL | 25% | w/w |
| 079 | Gauze | 50 uL | 5% | w/v |
| 080 | Gauze | 50 uL | 5% | w/v |
| 082 | Beads | 20 uL | 25% | w/w |
| 084 | Beads | 20 uL | 25% | w/w |
| 085 | Beads | 20 uL | 25% | w/w |
| 086 | Beads | 20 uL | 25% | w/w |
| 089 | Gauze | 50 uL | 5% | w/v |
| 090 | Gauze | 50 uL | 5% | w/v |

[1]All compounds except 055 were tested using an olfactometer arena. Compound 055 was tested using a petri dish arena.
[2]All compounds were tested in hexane except for compounds 067, 070 and 086 (hexane:methanol (1:1)), and compound 074 (dichloromethane:methanol (1:1)).

Results:

The results are presented in Tables 2 to 5, and for some exemplary compounds in The FIGURE.

All average repellency results reported in the table are based on 3 replicates for each reported trial, with each trial involving at least 3 observation periods. The observation periods were short-term (30 min), medium-term (1-2 hours), and long-term (24-48 hours). The "overall average" reported in the table represents the average for 3 replicates for 3 observation periods. At least one average (>50%) represents an average over 3 replicates for a single time period observation (for example, 1 hour).

The following compounds showed an overall average % R>80%:

Compound 067; Compound 079; Compound 089; Compound 041; Compound 044; Compound 048; Compound 069; Compound 035; Compound 090; Compound 040; Compound 073; Compound 086; Compound 057; Compound 061; Compound 003; Compound 024; Compound 074; Compound 058; Compound 054; Compound 078; Compound 014; Compound 082; Compound 080 and Compound 051.

TABLE 2

Repellency of Compounds of Formula (I): Summary of Results

| CHEMICAL INFORMATION | | | | % Repellency (% R)* | | | |
|---|---|---|---|---|---|---|---|
| | | | | Over all | At least One Average | At least One Time | |
| Compound # (STI-101) | Chemical Name | CAS # | Chemical structure | >50 % | >50 % | >50 % | Solvent |
| 001 | 4-oxo-2-pentenal | 5729-47-5 | O=CH-CH=CH-C(=O)-CH₃ | 57 | | | Hexane |

TABLE 2-continued

Repellency of Compounds of Formula (I): Summary of Results

| | CHEMICAL INFORMATION | | | % Repellency (% R)* | | | |
| --- | --- | --- | --- | --- | --- | --- | --- |
| | | | | | At least | At least | |
| | | | | Overall | One | One | |
| | | | | | Average | Time | |
| Compound # (STI-101) | Chemical Name | CAS # | Chemical structure | >50 % | >50 % | >50 % | Solvent |
| 003 | 4-oxo-2-heptenal | 55764-42-6 | | 90 | | | Hexane |
| 006 | (E)-6-hydroxyhex-4-en-3-one | 117646-30-7 | | | | 57 | Hexane |
| 008 | 2-oxoethyl propionate | 132041-24-8 | | | 53 | | Hexane |
| 010 | 2-oxobutyl formate | | | | 85 | | Hexane |
| 014 | 1-(furan-2-yl)propan-1-one | 3194-15-8 | | 94 | | | Hexane |
| 017 | allyl propionate | 2408-20-0 | | | | 90 | Hexane |
| 018 | N-(2-hydroxyethyl) propionamide | 18266-55-2 | | | | 69 | Hexane |
| 024 | Methyl undecyl ketone (2-tridecanone) | 593-08-8 | | 90 | | | Hexane |
| 025 | 3,4-dimethyl-2,5-hexanedione | 25234-79-1 | | 77 | | | Hexane |
| 026 | 3-Hexanone | 589-38-8 | | | | 100 | Hexane |
| 027 | 3,4-Hexanedione | 4437-51-8 | | 75 | | | Hexane |

TABLE 2-continued

Repellency of Compounds of Formula (I): Summary of Results

| | CHEMICAL INFORMATION | | | % Repellency (% R)* | | | |
|---|---|---|---|---|---|---|---|
| | | | | Over all | At least One Average | At least One Time | |
| Compound # (STI-101) | Chemical Name | CAS # | Chemical structure | >50 % | >50 % | >50 % | Solvent |
| 028 | 3-Nonanone | 925-78-0 | | | | 67 | Hexane |
| 031 | Vinyl propionate | 105-38-4 | | | | 100 | Hexane |
| 032 | N-Methylpropionamide | 1187-58-2 | | | | 100 | Hexane |
| 034 | Methyl 3-oxovalerate | 30414-53-0 | | | 94 | | Hexane |
| 035 | Furfuryl propionate | 623-19-8 | | 94 | | | Hexane |
| 037 | hexanal | 66-25-1 | | 79 | | | Hexane |
| 038 | trans-2-hexen-1-al | 6728-26-3 | | 72 | | | Hexane |
| 039 | trans-2-octenal | 2548-87-0 | | 78 | | | Hexane |
| 040 | (E)-1-(furan-2-yl)pent-1-en-3-one | 185256-75-1 | | 94 | | | Hexane |
| 041 | (E)-1-hydroxyoct-2-en-4-one | | | 98 | | | Hexane |
| 042 | (E)-6-hydroxyhept-4-en-3-one | | | 76 | | | Hexane |

TABLE 2-continued

Repellency of Compounds of Formula (I): Summary of Results

| Compound # (STI-101) | Chemical Name | CAS # | Chemical structure | Over all >50% | At least One Average >50% | At least One Time >50% | Solvent |
|---|---|---|---|---|---|---|---|
| 043 | N-allylpropionamide | 60205-24-5 | 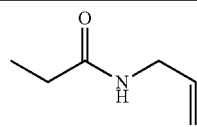 | 59 | | | Hexane |
| 044 | 6,10-dimethyl-5,9-undecadien-2-one | 3796-70-1 | 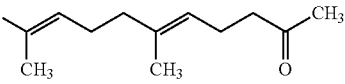 | 98 | | | Hexane |
| 045 | N-(2,2-dimethoxyethyl) propionamide | | 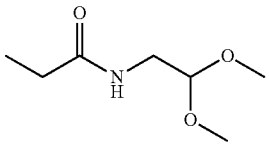 | 70 | | | Hexane |
| 046 | (E)-1-hydroxyhept-2-en-4-one | | 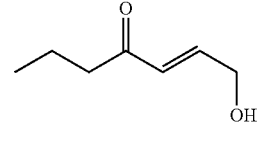 | 65 | | | Hexane |
| 048 | (E)-1-(furan-2-yl)-2-methylpent-1-en-3-one | 131375-70-7 | 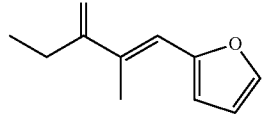 | 96 | | | Hexane |
| 049 | N-(2,2-dimethoxyethyl)-N-methylpropionamide | 118346-83-1 | 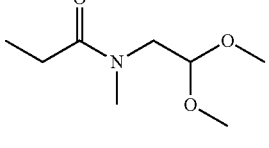 | 78 | | | Hexane |
| 051 | 4-heptanone | 123-19-3 | 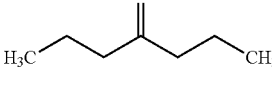 | 81 | | | Hexane |
| 052 | Methyl 4-oxobutanoate | 13865-19-5 | 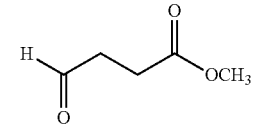 | | | 100 | Hexane |
| 053 | 4-(Dimethyl amino)-4-Oxobutanoic acid | 2564-95-6 | 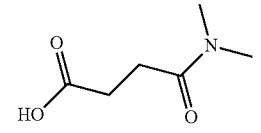 | 52 | | | Hexane |
| 054 | Methyl-2-oxobutanoate | 3952-66-7 | 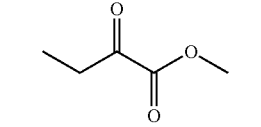 | 85 | | | Hexane |

TABLE 2-continued

Repellency of Compounds of Formula (I): Summary of Results

| | CHEMICAL INFORMATION | | | % Repellency (% R)* | | | |
|---|---|---|---|---|---|---|---|
| | | | | Over all | At least One Average | At least One Time | |
| Compound # (STI-101) | Chemical Name | CAS # | Chemical structure | >50 % | >50 % | >50 % | Solvent |
| 055 | Mono-ethyl succinate | 1070-34-4 | | 73§ | | | Hexane |
| 056 | Methyl trans-4-oxo-2-pentenoate | 2833-24-1 | | 53 | | | Hexane |
| 057 | Ethyl 3-methyl-4-oxocrotonate | 62054-49-3 | | 91 | | | Hexane |
| 058 | dimethyl fumarate | 624-49-7 | | 86 | | | Hexane |
| 060 | Tetrahydrofurfuryl propionate | 637-65-0 | | 78 | | | Hexane |
| 061 | 2-dodecanone | 6175-49-1 | | 90 | | | Hexane |
| 062 | 3-pentanone | 96-22-0 | | | | 89 | Hexane |
| 067 | (E)-oct-4-ene-3,6-dione | 188485-50-9 | | 100 | | | Hexane . . Methanol (1:1) |
| 068 | (E)-ethyl 4-oxohex-2-enoate | 118346-83-1 | | | 65 | | Hexane |
| 069 | 1-(furan-2-yl)ethanol | 4208-64-4 | | 94 | | | Hexane |

TABLE 2-continued

Repellency of Compounds of Formula (I): Summary of Results

| | | | | % Repellency (% R)* | | | |
|---|---|---|---|---|---|---|---|
| | | CHEMICAL INFORMATION | | Over all | At least One Average | At least One Time | |
| Compound # (STI-101) | Chemical Name | CAS # | Chemical structure | >50 % | >50 % | >50 % | Solvent |
| 070 | (E)-4-oxohex-2-enoic acid | 119677-86-0 | | 74 | | | Hexane : Methanol (1:1) |
| 071 | 1-(furan-2-yl)-2-methylpropan-1-ol | 4466-23-3 | | 57 | | | Hexane |
| 072 | 1-(furan-2-yl)-2-methylbutan-1-ol2-yl)-2-methylbutan-1-ol | 20906-93-8 | | 79 | | | Hexane |
| 073 | 1-(furan-2-yl) pentan-1-ol | 30478-77-4 | | 92 | | | Hexane |
| 074 | (E)-3-methylhept-3-ene-2,5-dione | | | 90 | | | Dichloromethane: Methanol (1:1) |
| 075 | 1-(furan-2-yl) propan-1-ol | 4208-61-1 | | 79 | | | Hexane |
| 076 | ethyl levulinate | 539-88-8 | | 69 | | | Hexane |
| 078 | 2-Furanmethanol, a-ethenyl- | 116914-87-5 | | 84 | | | Hexane |
| 079 | 6,6-diethoxyhex-4-yn-3-one | | | 100 | | | Hexane |

TABLE 2-continued

Repellency of Compounds of Formula (I): Summary of Results

| Compound # (STI-101) | Chemical Name | CAS # | Chemical structure | % Repellency (% R)* | | | Solvent |
|---|---|---|---|---|---|---|---|
| | | | | Over all >50% | At least One Average >50% | At least One Time >50% | |
| 080 | 2-Furyl methyl ketone | 1192-62-7 | | 81 | | | Hexane |
| 082 | 1-(2-furyl)-2-methyl-propan-1-one | 4208-53-1 | | 81 | | | Hexane |
| 084 | Furfuryl acetate | 623-17-6 | | 61 | | | Hexane |
| 085 | Ethyl 2-furoate | 614-99-3 | | 73 | | | Hexane |
| 086 | 2-butyrylfuran | 4208-57-5 | | 92 | | | Hexane . Methanol (1:1) |
| 089 | 1-furan-2-yl-2-methylbutan-1-one | 20895-17-4 | | 100 | | | Hexane |
| 090 | 1-Pentanone, 1-(2-furanyl)- | 3194-17-0 | | 94 | | | Hexane |

*Tested by olfactometer bioassay.
§Petri dish bioassay.

TABLE 3

Compounds Demonstrating an Overall Average Repellency > 50%

| Compound # (STI-101) | % R (Overall Av.) |
|---|---|
| 001 | 57 |
| 003 | 90 |
| 014 | 94 |
| 024 | 90 |
| 025 | 77 |
| 027 | 75 |
| 035 | 94 |
| 037 | 79 |
| 038 | 72 |
| 039 | 78 |
| 040 | 94 |
| 041 | 98 |
| 042 | 76 |
| 043 | 59 |
| 044 | 98 |
| 045 | 70 |
| 046 | 65 |
| 048 | 96 |
| 049 | 78 |
| 051 | 81 |
| 053 | 52 |
| 054 | 85 |

TABLE 3-continued

Compounds Demonstrating an Overall Average Repellency > 50%

| Compound # (STI-101) | % R (Overall Av.) |
|---|---|
| 055 | 73 |
| 056 | 53 |
| 057 | 91 |
| 058 | 86 |
| 060 | 78 |
| 061 | 90 |
| 067 | 100 |
| 069 | 94 |
| 070 | 74 |
| 071 | 57 |
| 072 | 79 |
| 073 | 92 |
| 074 | 90 |
| 075 | 79 |
| 076 | 69 |
| 078 | 84 |
| 079 | 100 |
| 080 | 81 |
| 082 | 81 |
| 084 | 61 |
| 085 | 73 |
| 086 | 92 |
| 089 | 100 |
| 090 | 94 |

TABLE 4

Compounds Demonstrating At Least One Average Repellency > 50%*

| Compound # (STI-101) | % Repellency | | | |
|---|---|---|---|---|
| | T1 | T2 | T3 | Overall Av. |
| 008 | 12 | 53 | 17 | 27 |
| 010 | 85 | 42 | 8 | 45 |
| 018 | 69 | 69 | 11 | 50 |
| 068 | 30 | 32 | 65 | 43 |
| 034 | 81 | 94 | −94 | 27 |

*But overall average repellency of < 50%

TABLE 5

Compounds Demonstrating At Least One Repellency >50%*

| Compound # (STI-101) | Repetition | % Repellency | | | |
|---|---|---|---|---|---|
| | | T1 | T2 | T3 | Overall Av. |
| 006 | 1 | −25 | −60 | 0 | −49 |
| | 2 | −71 | −71 | 57 | |
| | 3 | −90 | −90 | −89 | |
| | Average | −62 | −74 | −11 | |
| 017 | 1 | 0 | 90 | 63 | 4 |
| | 2 | −60 | −83 | −75 | |
| | 3 | 0 | 33 | 67 | |
| | Average | −20 | 13 | 18 | |
| 026 | 1 | 83 | 100 | −67 | 15 |
| | 2 | −50 | −50 | −100 | |
| | 3 | 100 | 60 | 60 | |
| | Average | 44 | 37 | −36 | |
| 028 | 1 | 0 | 0 | −43 | −10 |
| | 2 | −33 | −33 | −43 | |
| | 3 | 0 | 0 | 67 | |
| | Average | −11 | −11 | −6 | |
| 031 | 1 | 100 | 100 | −60 | 8 |
| | 2 | 60 | 60 | −80 | |
| | 3 | −25 | −25 | −60 | |
| | Average | 45 | 45 | −67 | |
| 032 | 1 | 75 | 80 | 100 | −9 |
| | 2 | −33 | −100 | −100 | |
| | 3 | 75 | −100 | −75 | |
| | Average | 39 | −40 | −25 | |
| 052 | 1 | 33 | −100 | −100 | −17 |
| | 2 | 0 | −50 | −33 | |
| | 3 | 0 | 0 | 100 | |
| | Average | 11 | −50 | −11 | |
| 062 | 1 | 71 | 71 | 89 | 10 |
| | 2 | −83 | −60 | 60 | |
| | 3 | −20 | −20 | −20 | |
| | Average | −11 | −3 | 43 | |

*But average repellency (one time or overall) of <50%

Example 2

Repellency of Combinations of Compounds of Formula (I)

To determine whether compounds could be combined in the repellent compositions, compounds 14 and 35 were each tested at a concentration of 5% (w/w), and as a combination comprising each compound at a concentration of 2.5% (w/w). The formulations were tested as described in Example 1 using the olfactometer configuration. The results are shown in Table 6 and demonstrate that combining the compounds did not adversely affect their repellent activity.

TABLE 6

Repellency of a Combination of Compounds 14 and 35

| Compound # (STI-101) | % R (Overall Average) |
|---|---|
| Combination I (014 + 035) | 94 |
| 035 | 95 |
| 014 | 71 |

Example 3

Formulations of Compound 35

Compound 35 was formulated as a spray formulation in which the compound was dissolved in isopropyl alcohol (IPA) at concentrations of 1%, 2.5% and 5%.

In addition, compound 35 was tested on plastic slow-release beads. The beads were cured with either: 1) 20% (w/w) neat compound 35, or 2) 20% (w/w) of a 1:1 mixture of compound 35 and wintergreen oil (methyl salicylate).

The formulations were tested as described in Example 1 using the box configuration. The results are shown in Table 7 and demonstrate that compound 35 showed excellent repellency in both formulation formats and at all concentrations tested.

TABLE 7

Repellency of Formulations of Compound 35

| Formulation | Concentration of Compound 35 (w/w) | % R (Overall Average) |
|---|---|---|
| IPA spray | 1% | 92 |
|  | 2.5% | 94 |
|  | 5% | 100 |
| Plastic beads | 20% | 100 |
|  | 10% + 10% wintergreen oil | 100 |

Example 4

Additional Exemplary Formulations

The following represent proposed formulation formats for the compositions of the invention.

Formulation 1: Aerosol or pump-spray application of repellent substance for application to luggage and clothing. In the case of luggage, application of repellent is intended to prevent the migration of bed bugs from an infested location to non-infested infested location (e.g., infested hotel room to residence). In the case of clothing, police, paramedics, fire fighters have expressed a strong need for a suitable repellent for application to clothing before they enter premises that may house a bed bug infestation.

Formulation 2: Dryer sheet or ball application where a repellent impregnated substrate device is employed to distribute repellent substance to clothing and bedding.

Formulation 3: Slow release polymer beads contained in breathable sachet for placement inside of luggage or for placement in room areas were protection from bed bugs is desired, e.g., near a bed. In addition to beads, slow release formulations may include wax substrates that slowly release vapours or are induced to release vapours using a small heating element (e.g., "plug-ins").

Formulation 4: Timed release application utilizing a device that triggers release of aerosol and specific intervals or time of day (similar to devices used to dispense household fragrances at timed intervals).

Example 5

Synthesis of Compound 10

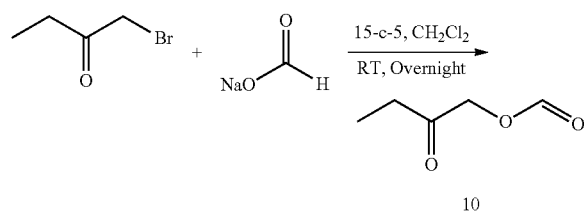

Compound 10 was prepared according to the scheme above. Briefly, sodium formate (0.27 g, 4.0 mmol) was ground with a pestle and added to a dry 10 mL round-bottom flask under nitrogen. Dry dichloromethane (5 mL) was added followed by 15-crown-5 (0.65 g, 3.0 mmol). Once fully mixed, 1-bromo-2-butanone (0.30 g, 2.0 mmol) was added and the reaction stirred at room temperature overnight. The solids were removed by filtration, and the solution was concentrated. Flash chromatography using hexane/ethyl acetate as an eluent yielded compound 10 (0.10 g, 43%) as a colourless oil.

Example 6

Synthesis of Compound 45

In a 250 mL round-bottom flask, 2-aminobenzaldehyde dimethyl acetal (3.4 mL, 31 mmol, 1.5 equiv.) and triethylamine (5.7 mL, 41 mmol, 2.0 equiv.) were dissolved in freshly distilled dichloromethane (60 mL) and the solution was cooled to 0° C. A solution of propionyl chloride (1.8 mL, 20 mmol, 1.0 equiv.) in freshly distilled dichloromethane (60 mL) was added dropwise with a syringe. The reaction mixture was further stirred at 0° C. for 3 hours, and allowed to warm up to room temperature. The mixture was then supported on silica gel and filtered through a silica gel plug, washing the filter cake with ethyl acetate (200 mL). The filtrate was then concentrated by rotary evaporation yielding 3.48 g (quantitative yield) of compound 45 as a slightly yellow oil. NMR showed pure product.

Example 7

Synthesis of Compound 46

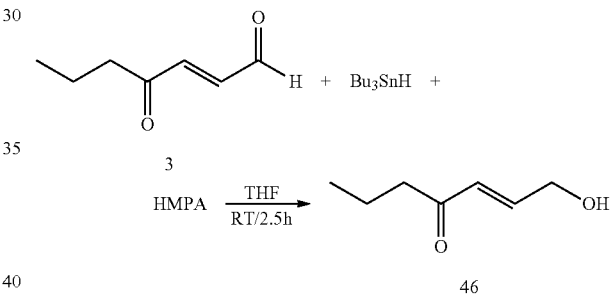

Compound 46 was prepared according to the scheme shown above using equimolar amounts of compound 3, Bu$_3$SnH and HMPA. Solvent was removed by rotary evaporation and the residue submitted to flash chromatography (2:1 hexane:ethyl acetate). A 20% yield of compound 46 was obtained.

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

The embodiments of the invention in which an exclusive property or privilege is claimed are defined as follows:

1. A method for repelling bedbugs comprising contacting the bedbugs with, or applying to an area known or suspected of containing bedbugs, a composition comprising a carrier and one or more compounds of general formula (I):

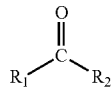 (I)

wherein: $R_1$ is selected from the group consisting of: $C_1$-$C_4$ alkyl and alkoxy, and wherein $R_2$ is a substituent of general formula (III):

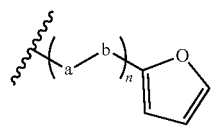 (III)

wherein a is —O— and b is $CH_2$, or a-b represents —CR'=CR"—, wherein R' is H or $C_1$-$C_4$ alkyl, R" is H, and n=0 or 1.

2. The method according to claim 1, wherein the area known or suspected of containing bedbugs comprises a bed, boxspring, mattress, bed linen, or a combination thereof.

3. The method according to claim 1, wherein the applying comprises spraying the area with the composition.

4. The method according to claim 1, wherein the applying comprises placing into the area the composition absorbed onto or impregnated into a solid matrix.

5. A method for repelling bedbugs comprising contacting the bedbugs with, or applying to an area known or suspected of containing bedbugs, a composition comprising a carrier and one or more compounds of general formula (I):

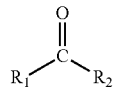 (I)

wherein:

$R_1$ is selected from the group consisting of: $C_2$ alkyl, $C_4$ alkyl and $C_1$-$C_4$ alkoxy, and wherein $R_2$ is a substituent of general formula (III):

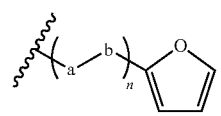 (III)

wherein a-b represents —CR'=CR"—, and wherein R' is H or $C_1$-$C_4$ alkyl and R" is H, and n=0 or 1.

6. A method for repelling bedbugs comprising contacting the bedbugs with, or applying to an area known or suspected of containing bedbugs, a composition comprising a carrier and the following compound:

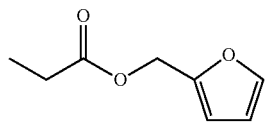

* * * * *